United States Patent
Hirota

(10) Patent No.: US 9,186,051 B2
(45) Date of Patent: Nov. 17, 2015

(54) IMAGE PROCESSING DEVICE, COMPUTER-READABLE RECORDING DEVICE, AND IMAGE PROCESSING METHOD

(75) Inventor: Masashi Hirota, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 203 days.

(21) Appl. No.: 13/351,342

(22) Filed: Jan. 17, 2012

(65) Prior Publication Data

US 2012/0114203 A1 May 10, 2012

Related U.S. Application Data

(63) Continuation of application No. PCT/JP2010/061977, filed on Jul. 15, 2010.

(30) Foreign Application Priority Data

Jul. 23, 2009 (JP) ................................. 2009-172435

(51) Int. Cl.
*G06K 9/00* (2006.01)
*A61B 1/04* (2006.01)
(Continued)

(52) U.S. Cl.
CPC ................ *A61B 1/041* (2013.01); *G06K 9/342* (2013.01); *G06K 9/4671* (2013.01); *G06T 7/0016* (2013.01); *G06T 2207/10068* (2013.01); *G06T 2207/30028* (2013.01); *G06T 2207/30092* (2013.01)

(58) Field of Classification Search
None
See application file for complete search history.

(56) References Cited

U.S. PATENT DOCUMENTS 6,654,728 B1 * 11/2003 Li et al. .............................. 706/2
6,801,645 B1 * 10/2004 Collins et al. ................. 382/130
(Continued)

FOREIGN PATENT DOCUMENTS

| JP | 2005-131031 | 5/2005 |
| JP | 2005-192880 | 7/2005 |

(Continued)

OTHER PUBLICATIONS

Cigdem Demir, S. Humayun Gultekin, Bulent Yener. "Augmented cell-graphs for automated cancer diagnosis" Bioinformatics , vol. 21 . 2005.*

(Continued)

*Primary Examiner* — Bhavesh Mehta
*Assistant Examiner* — Oneal A Mistry
(74) *Attorney, Agent, or Firm* — Scully, Scott, Murphy & Presser, P.C.

(57) ABSTRACT

An image processing device includes: an interest area detector that detects interest areas included in a time-series image group captured in time series; a calculation processing unit that calculates feature amounts indicative of features of the interest areas; an area classification unit that classifies the interest areas into area groups, based on the feature amounts of the interest areas and time-series positions of time-series images including the interest areas; a group feature amount calculation unit that calculates a group feature amount indicative of a feature of each of the area groups; an area selection unit that selects one or more representative areas of the interest areas belonging to the area groups, from among the area groups; and a representative image output unit that outputs one or more representative images including the representative areas in the time-series image group.

21 Claims, 11 Drawing Sheets

(51) Int. Cl.
*G06T 7/00* (2006.01)
*G06K 9/34* (2006.01)
*G06K 9/46* (2006.01)

(56) References Cited

U.S. PATENT DOCUMENTS

| | | | |
|---|---|---|---|
| 7,088,850 B2 * | 8/2006 | Wei et al. | 382/128 |
| 7,272,251 B2 * | 9/2007 | Acar et al. | 382/128 |
| 7,496,228 B2 * | 2/2009 | Landwehr et al. | 382/170 |
| 7,720,267 B2 * | 5/2010 | Fuchs et al. | 382/128 |
| 7,756,309 B2 * | 7/2010 | Gholap et al. | 382/128 |
| 7,783,094 B2 * | 8/2010 | Collins et al. | 382/128 |
| 7,949,181 B2 * | 5/2011 | Padfield et al. | 382/164 |
| 7,953,264 B2 * | 5/2011 | Levenson et al. | 382/128 |
| 8,000,773 B2 * | 8/2011 | Rousso et al. | 600/436 |
| 8,014,576 B2 * | 9/2011 | Collins et al. | 382/128 |
| 2005/0197567 A1 * | 9/2005 | Qian et al. | 600/425 |
| 2007/0195165 A1 * | 8/2007 | Hirakawa | 348/75 |

FOREIGN PATENT DOCUMENTS

| | | |
|---|---|---|
| JP | 2005-236993 | 9/2005 |
| JP | 2006-280792 | 10/2006 |
| JP | 2006-320650 | 11/2006 |
| JP | 2007-006129 | 1/2007 |

OTHER PUBLICATIONS

Shingo Iwano, Tatsuya Nakamura, Yuko Kamioka, Takeo Ishigaki. "Computer-aided diagnosis: A shape classification of pulmonary nodules imaged by high-resolution CT" Elsevier , vol. 29. 2005.*
International Search Report dated Aug. 24, 2010, issued in PCT/JP2010/061977.

* cited by examiner

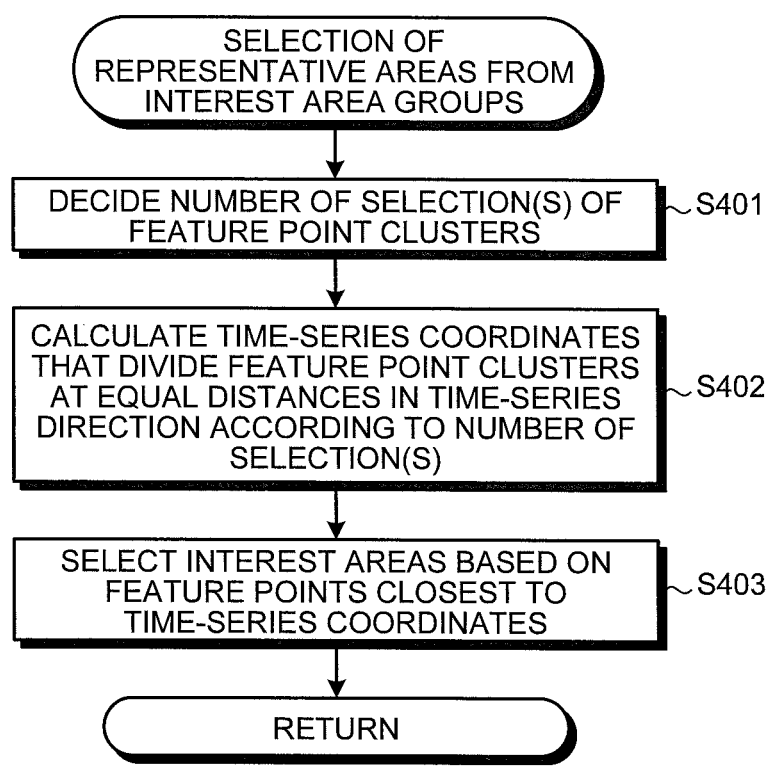

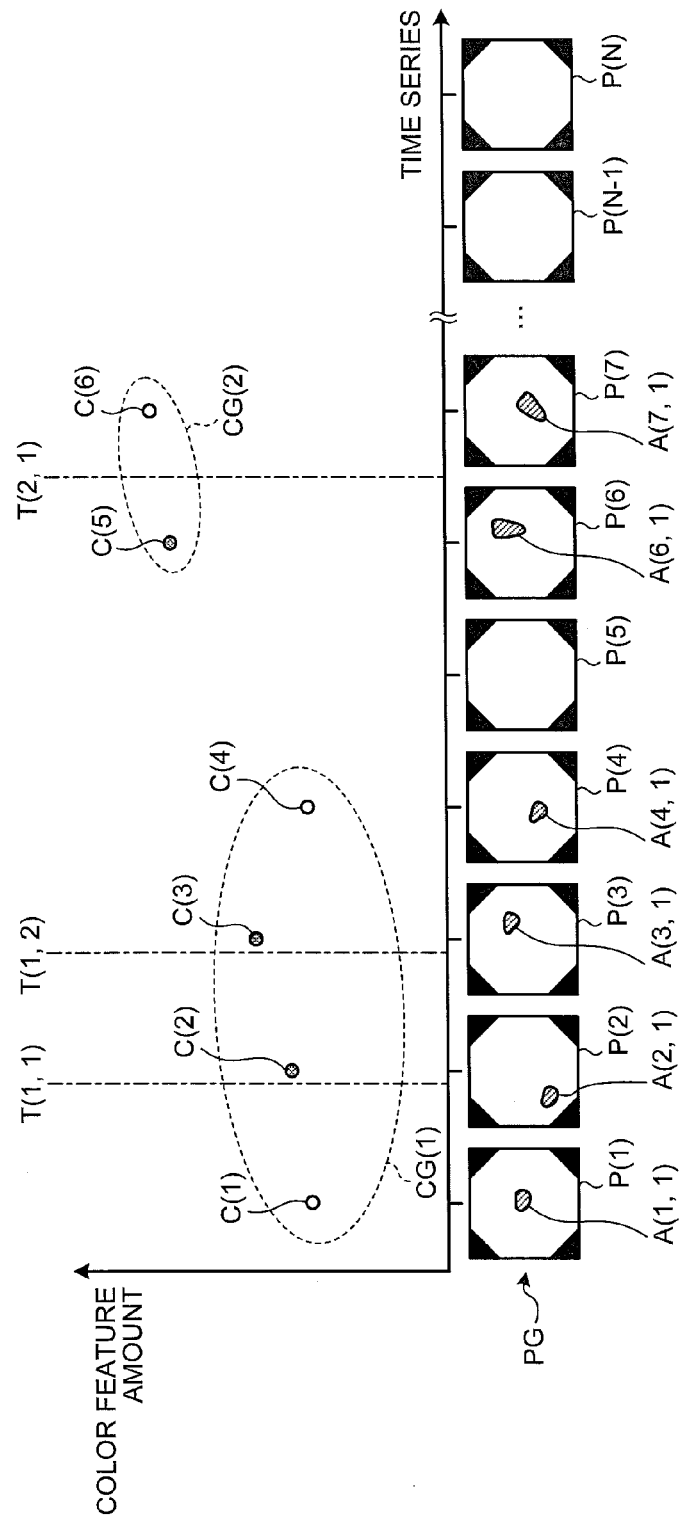

IMAGE PROCESSING DEVICE, COMPUTER-READABLE RECORDING DEVICE, AND IMAGE PROCESSING METHOD

CROSS-REFERENCE TO RELATED APPLICATIONS

This application is a continuation of PCT international application Ser. No. PCT/JP2010/061977 filed on Jul. 15, 2010 which designates the United States, incorporated herein by reference, and which claims the benefit of priority from Japanese Patent Application No. 2009-172435, filed on Jul. 23, 2009, incorporated herein by reference.

BACKGROUND OF THE INVENTION

1. Field of the Invention

The present invention relates to an image processing device, an image processing program, and an image processing method, particularly to an image processing device, an image processing program, and an image processing method in which a group of representative images to be paid attention is selected from groups of time-series images of insides of lumens or the like of a subject captured in time series.

2. Description of the Related Art

Conventionally, electronic imaging devices for capturing images of an object have emerged in various forms such as digital cameras, digital video cameras, and the like. The electronic imaging devices are capable of continuously capturing images of an object in time series, and a group of continuously captured images of the object in time series (hereinafter, referred to as a group of time-series images) can be observed in sequence by displaying on a display device such as a liquid crystal display.

In recent years, particularly in the medical field, there has been suggested a capsule endoscope that is capable of capturing in-vivo images of a subject such as a patient, sequentially in time series. The capsule endoscope is a medical device that includes a capturing function, a wireless communication function, and the like, in a small capsule-shaped casing which can be swallowed by a subject. When being swallowed by a subject, the capsule endoscope captures images of inside of the digestive tract (hereinafter, referred to as in-vivo images) sequentially in time series at a predetermined capturing rate, while moving in the digestive tract by peristaltic motion or the like, and transmits the obtained in-vivo images sequentially in a wireless manner to a receiving device on the outside of the subject. After having transmitted a group of in-vivo images, the capsule endoscope in the subject is finally excreted out of the body of the subject. The group of in-vivo images captured by the capsule endoscope is one example of a group of time-series images.

In this arrangement, the number of images in a group of in-vivo images captured by the capsule endoscope generally becomes as enormous as several tens of thousands. For example, the capsule endoscope continuously captures in-vivo images in time series, at a capturing rate of 2 to 4 frames per second, for a period of time between the instant when the capsule endoscope is orally ingested and the instant when the same is excreted together with excretion or the like out of the body (about 8 to 10 hours).

SUMMARY OF THE INVENTION

An image processing device according to an aspect of the present invention includes: an interest area detector that detects interest areas included in a time-series image group captured in time series; a calculation processing unit that calculates feature amounts indicative of features of the interest areas; an area classification unit that classifies the interest areas into area groups, based on the feature amounts of the interest areas and time-series positions of time-series images including the interest areas; a group feature amount calculation unit that calculates a group feature amount indicative of a feature of each of the area groups; an area selection unit that selects one or more representative areas of the interest areas belonging to the area groups, from among the area groups; and a representative image output unit that outputs one or more representative images including the representative areas in the time-series image group.

The time-series positions of time-series images refer to time-series positions of time-series images in a time-series image group, which indicate information on timing at which the time-series images are captured. The information on timing may be information on time (seconds, minutes, hours, and the like) elapsed from the first time-series image out of the time-series images constituting a time-series image group captured in time series, or may be information on a capturing time (hour/minute/second). In either case, time-series images captured in time series can be arranged in time-series based on the information. In addition, the interest area refers to an area to be paid attention with a high need for an observer to observe. If a time-series image group captured in time series is an in-vivo image group showing the inside of a human body, for example, interest areas in the group may be mucosal areas or lesion areas, for example. Meanwhile, areas with a lower need for an observer to observe correspond to non-interest areas. If a time-series image group captured in time series is an in-vivo image group showing the inside of a human body, for example, the non-interest areas in the group may be areas of bubbles, stools, or the like.

A computer-readable recording device with an executable program stored thereon, wherein the program instructs a processor to perform: detecting interest areas included in a time-series image group captured in time series; calculating feature amounts indicative of features of the interest areas; classifying the interest areas into area groups, based on the feature amounts of the interest areas and time-series positions of time-series images including the interest areas; calculating a group feature amount indicative of a feature of each of the area groups; selecting one or more representative areas of the interest areas belonging to the area groups, from among the area groups; and outputting one or more representative images including the representative areas in the time-series image group.

An image processing program according to still another aspect of the present invention includes: detecting interest areas included in a time-series image group captured in time series; calculating feature amounts indicative of features of the interest areas; classifying the interest areas into area groups, based on the feature amounts of the interest areas and time-series positions of time-series images including the interest areas; calculating a group feature amount indicative of a feature of each of the area groups; selecting one or more representative areas of the interest areas belonging to the area groups, from among the area groups; and outputting one or more representative images including the representative areas in the time-series image group.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 11 is a flowchart illustrating an example of a processing procedure of selecting representative areas from interest area groups in the second embodiment; and FIG. 12 is a schematic diagram describing the process of selecting representative areas in the second embodiment.

DETAILED DESCRIPTION OF THE PREFERRED EMBODIMENTS

Embodiments of an image processing device, an image processing program, and an image processing method in the present invention will be described in detail with reference to the drawings. In the following description, an in-vivo image group of the inside of the body of a subject captured in time series by a capsule endoscope, is shown as an example of a time-series image group captured in time series, and the image processing device, the image processing program, and the image processing method, configured to output in-vivo images including interest areas to be observed as representative images from the in-vivo image group, are described. However, the present invention is not limited to these embodiments.

First Embodiment

Figure 1:
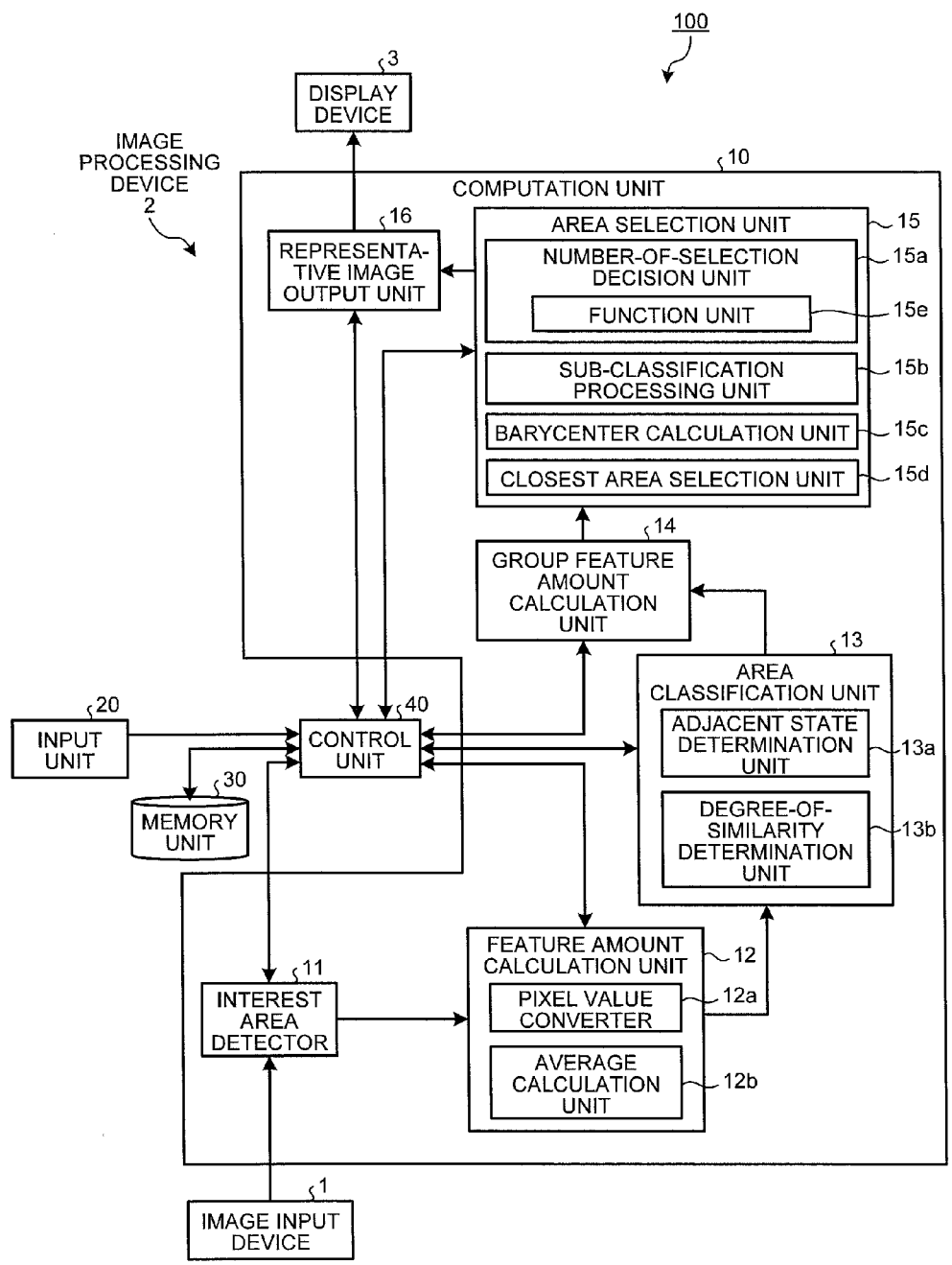
FIG. 1 is a block diagram schematically illustrating a configuration of an image display system including an image processing device according to a first embodiment of the present invention.

FIG. 1 is a block diagram schematically illustrating a configuration example of an image display system including the image processing device according to a first embodiment of the present invention. As illustrated in FIG. 1, an image display system 100 according to the first embodiment includes: an image input device 1 for inputting an in-vivo image group of a subject; an image processing device 2 that performs various kinds of image processing to output one or more frames of in-vivo images including an interest area from the in-vivo image group input by the image input device 1; and a display device 3 that displays one or more frames of in-vivo images output by the image processing device 2.

The image input device 1 is a device for inputting an in-vivo image group of a subject into the image processing device 2. Specifically, the image input device 1 is a data input interface in/from which a portable recording medium can be attached and detached. A recording medium storing an in-vivo image group of a subject captured by a capsule endoscope or the like, can be detachably inserted into the image input device 1. The image input device 1 takes in the in-vivo image group from the recording medium and inputs the same into the image processing device 2.

The image processing device 2 performs various kinds of image processing to extract in-vivo images including interest areas from the in-vivo image group input by the image input device 1. Specifically, the image processing device 2 acquires the in-vivo image group of a subject from the image input device 1, and performs image processing on in-vivo images included in the acquired in-vivo image group, and extracts one or more frames of in-vivo images including interest areas from the in-vivo image group. The image processing device 2 outputs one or more frames of in-vivo images including interest areas, as representative images of the in-vivo images in the in-vivo image group, to the display device 3. A detailed configuration of the image processing device 2 will be described later.

In the first embodiment, the interest areas included in the in-vivo image group of the subject refer to in-vivo areas (in-vivo sites) to be noted and observed by an observer such as a doctor or a nurse, and for example, the interest areas may be lesion areas or mucosal areas in a digestive tract, body tissue areas after medical treatment, or the like.

The display device 3 functions as a user interface that displays output of one or more frames of in-vivo images including the interest areas in the in-vivo image group. Specifically, the display device 3 can be realized using a desired display such as a CRT display or a liquid crystal display. The display device 3 acquires one or more frames of representative images extracted by the image processing device 2 from the in-vivo image group.

The representative images displayed on the display device 3 are in-vivo images of interest areas such as lesion areas in the inside of the body of a subject. The observer can observe the displayed representative images and examine the inside of the digestive tract of a subject.

Next, the configuration of the image processing device 2 according to the first embodiment of the present invention will be described below in detail. As illustrated in FIG. 1, the image processing device 2 according to the first embodiment includes a computation unit 10 that performs arithmetic processing or the like on the in-vivo images in the in-vivo image group; an input unit 20 that inputs various kinds of information such as setting information required for image processing; a memory unit 30 that stores various kinds on data of in-vivo images and the like; and a control unit 40 that controls components of the image processing device 2.

The computation unit 10 performs various kinds of arithmetic processing on the in-vivo images in the in-vivo image group input by the image input device 1. Specifically, the computation unit 10 includes an interest area detector 11 that detects interest areas included in the in-vivo image group; a feature amount calculation unit 12 that calculates feature amounts of the interest areas detected by the interest area detector 11; and an area classification unit 13 that classifies the interest areas according to the feature amounts calculated by the feature amount calculation unit 12 and time-series positions of the in-vivo images including the interest areas. The computation unit 10 includes a group feature amount calculation unit 14 that calculates feature amounts of the area groups to which the interest areas classified by the area classification unit 13 belong (hereinafter, referred to as group feature amounts); an area selection unit 15 that selects one or more representative areas representing the interest areas belonging to the area groups; and a representative image output unit 16 that outputs one or more representative images including the representative areas selected by the area selection unit 15.

The interest area detector 11 detects the interest areas included in the in-vivo image group. Specifically, the interest area detector 11 acquires an in-vivo image group PG including total N images from the image input device 1, and assigns frame numbers $j(1 \leq j \leq N)$ to in-vivo images P(j) in the acquired in-vivo image group PG in time series. The interest area detector 11 detects interest areas A(j, t) such as lesion areas from the in-vivo images P(j), based on feature amounts of the in-vivo images P(j) such as color information. The interest area detector 11 transmits results of detection of the interest areas A(j, t) and the in-vivo image group PG to the feature amount calculation unit 12. In this arrangement, t denotes an index (identifier) for identifying one or more interest areas A(j, t) included in one frame of an in-vivo image P(j).

The feature amount calculation unit 12 functions as a calculation processing unit that calculates feature amounts indicative of features of the interest areas A(j, t) detected by the interest area detector 11 from the in-vivo images P(j). Specifically, the feature amount calculation unit 12 includes a pixel value converter 12a that converts pixel values of pixels belonging to the interest areas A(j, t) into values of a desired color space; and an average calculation unit 12b that calculates averages of pixel values of the interest areas A(j, t) converted by the pixel value converter 12a.

The pixel value converter 12a converts values of pixels belonging to the interest areas A(j, t), for example, values of color space of red, green, and blue (RGB), into values of $L^*a^*b^*$ space, for each of the interest areas detected by the interest area detector 11 from the in-vivo image group PG. The average calculation unit 12b calculates averages of values of the $L^*a^*b^*$ space converted and output by the pixel value converter 12a as feature amounts of the interest areas A(j, t), for example, color feature amounts. The thus calculated feature amounts of interest areas A(j, t) are transmitted to the area classification unit 13 together with the in-vivo image group PG.

The area classification unit 13 classifies the interest areas A(j, t) into area groups, based on the feature amounts of the interest areas A(j, t) calculated by the feature amount calculation unit 12, and on the time-series positions of the in-vivo images P(j) including the interest areas A(j, t) detected by the interest area detector 11. Specifically, the area classification unit 13 includes an adjacent state determination unit 13a that determines a time-series adjacent state of the interest areas A(j, t), and a degree-of-similarity determination unit 13b that determines the degree of similarity indicative of similarity in feature amount between the interest areas A(j, t).

The adjacent state determination unit 13a determines whether a plurality of interest areas A(j, t) detected by the interest area detector 11 from the in-vivo image group PG are adjacent to each other in time series. The time-series adjacent state of the interest areas A(j, t) determined by the adjacent state determination unit 13a indicates a time-series distribution state of the interest areas A(j, t) in a feature space formed by a coordinate axis of feature amount and a time-series coordinate axis of the interest areas A(j, t).

The degree-of-similarity determination unit 13b determines the degree of similarity indicative of similarity in feature amount (e.g. color feature amount) between a plurality of interest areas A(j, t) calculated by the feature amount calculation unit 12. The degree of similarity between the interest areas A(j, t) determined by the degree-of-similarity determination unit 13b indicates a distribution state of feature amounts of the interest areas A(j, t) in the foregoing feature space.

In this arrangement, the area classification unit 13 grasps a time-series distribution state of the interest areas A(j, t) in the feature space, based on results of the foregoing time-series adjacent condition determination of the interest areas A(j, t). The area classification unit 13 also grasps a distribution state of feature amounts of the interest areas A(j, t) in the feature space, based on results of the foregoing determination on the degree of similarity between the interest areas A(j, t). The area classification unit 13 classifies the interest areas A(j, t) into area groups, based on the grasped distribution state and time-series distribution state of feature amounts of the interest areas A(j, t). In such a manner, the area classification unit 13 classifies the interest areas A(j, t) that fall within a predetermined threshold range of distribution of feature amounts in the feature space and are adjacent or identical to each other in time series, into the same area group. The area classification unit 13 transmits results of the group classification of the interest areas A(j, t) and the in-vivo image group PG, to the group feature amount calculation unit 14.

The group feature amount calculation unit 14 calculates group feature amounts indicative of features of area groups of the interest areas A(j, t) classified by the area classification unit 13. Specifically, the group feature amount calculation unit 14 acquires the in-vivo image group PG from the area classification unit 13, and calculates dispersion of feature amounts in the feature space of the interest areas A(j, t) belonging to the area groups in the acquired in-vivo image group PG. Then, the group feature amount calculation unit 14 calculates group feature amounts of the area groups, based on results of the dispersion calculation of calculated feature amounts of the area groups.

Dispersion of feature amounts of the interest areas A(j, t) in the feature space refers to dispersion based on averages of color feature amounts of the interest areas A(j, t) calculated by the average calculation unit 12b, that is, averages of values of the $L^*a^*b^*$ space belonging to the interest areas A(j, t). The group feature amount calculation unit 14 calculates respective group feature amounts of the area groups, by totalizing the foregoing dispersion of feature amounts of the interest areas A(j, t) in each of the area groups. The group feature amount calculation unit 14 transmits results of the calculation of group feature amounts and the in-vivo image group PG to the area selection unit 15.

The area selection unit 15 selects one or more representative areas of the interest areas A(j, t) from the area groups, based on the group feature amounts calculated by the group feature amount calculation unit 14. Specifically, the area selection unit 15 includes: a number-of-selection decision unit 15a deciding the numbers of selections of representative areas from the area groups; a sub-classification processing unit 15b that sub-classifies a plurality of interest areas A(j, t) included in the area groups, into the same number of similarity groups as the number of selection(s); a barycenter calculation unit 15c that calculates barycenters of the similarity groups after the sub-classification; and a closest area selection unit 15d that selects interest areas closest to the barycenters of the similarity groups for the respective similarity groups.

The number-of-selection decision unit 15a includes a function unit 15e. The function unit 15e holds in advance a function indicative of a relationship between the numbers of selected representative areas and the group feature amounts. If a group feature amount is input, the number-of-selection decision unit 15a calculates the rates of abstract for the area groups, based on the input group feature amount and the previously held function. In this arrangement, the rates of abstract calculated by the function unit 15e constitute values for deciding what % of the interest areas A(j, t) belonging to one area group to be selected. In addition, the function held by the function unit 15e may be preset at the function unit 15e or may be set at the function unit 15e by the control unit 40 based on function information input from the input unit 20.

Specifically, the number-of-selection decision unit 15a multiplies the rates of abstract calculated by the function unit 15e for the area groups by the total numbers of the interest areas A(j, t) in the area groups, and then rounds off results of the multiplication to the closest whole numbers, thereby deciding the numbers of representative areas to be selected from the area groups.

The sub-classification processing unit 15b sub-classifies a plurality of interest areas A(j, t) in the area groups in the in-vivo image group PG, into similarity groups with further similar features. Specifically, the sub-classification processing unit 15b sub-classifies the interest areas A(j, t) in the area groups, into the same number of the similarity groups as the number of selection(s) decided by the number-of-selection decision unit 15a, based on the degrees of similarity in feature between a plurality of interest areas A(j, t) included in the area groups in the in-vivo image group PG.

The degree of similarity in feature between the interest areas A(j, t) may be the degree of similarity in color feature amount between the interest areas A(j, t) calculated by the foregoing average calculation unit 12b, for example. If the degree of similarity in feature between the interest areas A(j, t) is the degree of similarity in color feature amount, the interest areas A(j, t) in the similarity groups sub-classified by the sub-classification processing unit 15b become interest areas which are further similar in color feature amount, as compared with the interest areas A(j, t) in the area groups before the sub-classification process.

The barycenter calculation unit 15c calculates barycenters of feature amounts of a plurality of interest areas A(j, t) included in the similarity groups sub-classified by the sub-classification processing unit 15b. In this arrangement, the barycenters of feature amounts of the interest areas A(j, t) in the similarity group are coordinate points in a feature space based on an average of feature amounts of a plurality of interest areas A(j, t) included in the same similarity group and time-series positions of the interest areas A(j, t). In addition, the average of feature amounts of the interest areas A(j, t) may be an average of color feature amounts calculated by the average calculation unit 12b, for example.

The closest area selection unit 15d selects the interest area closest to the barycenter of feature amounts calculated by the barycenter calculation unit 15c, from a plurality of interest areas A(j, t) included in the foregoing similarity group. Specifically, the closest area selection unit 15d selects the interest area A(j, t) with a feature amount with a minimum Euclidean distance from the barycenter of feature amounts in the feature space, for each of the similarity groups. Specifically, the closest area selection unit 15d selects the interest area A(j, t) corresponding to a coordinate point in the feature space closest to the foregoing barycenter of feature amounts, for each of the similarity groups.

The thus configured area selection unit 15 sets the interest area A(j, t) selected by the closest area selection unit 15d as a representative area for each of the similarity groups sub-classified by the sub-classification processing unit 15b, thereby to select the same number of representative area(s) for each of the area groups as the number of selection(s) decided by the number-of-selection decision unit 15a from the in-vivo image group PG. The area selection unit 15 transmits results of the selection of representative area(s) for each of the area groups and the in-vivo image group PG, to the representative image output unit 16. In addition, the area selection unit 15 sets the number of selection as "1" for an area group with the number of selection of less than 1, thereby to select at least one interest area A(j, t) from the area group.

The representative image output unit 16 outputs one or more representative images including a representative area in the in-vivo image group PG. Specifically, the representative image output unit 16 acquires the in-vivo image group PG having been subjected to the foregoing representative area selection process, and extracts in-vivo images including the representative images selected by the area selection unit 15 from the acquired representative image group PG. The representative image output unit 16 outputs one or more frames of extracted in-vivo images including the representative images as representative images to be output (e.g. to be displayed), to the display device 3.

In addition, if a plurality of representative areas is included in the in-vivo image group PG, the representative image output unit 16 outputs the representative image groups as a plurality of in-vivo image groups including the plurality of representative areas, to the display device 3. One or more frames of representative images output by the representative image output unit 16 are displayed as in-vivo images to be observed on the display device 3 as described above.

The input unit 20 is implemented using an input device and the like exemplified by a keyboard and a mouse, for example. The input unit 20 inputs various kinds of information to the control unit 40 of the image processing device 2, in accordance with an input operation by an observer (user) such as a doctor or a nurse. Various kinds of information input by the input unit 20 into the control unit 40 may be instructions for the control unit 40 to start or terminate operation of the image processing device 2, function information set to the foregoing function unit 15e, various parameters required for image processing by the image processing device 2, and the like, for example.

The memory unit 30 is implemented using various storage media for storing information rewritably, such as RAM, EEPROM, flash memory, or a hard disk. The memory unit 30 stores various kinds of information to be stored under instruction from the control unit 40, and transmits information to be read from various kinds of stored information under instructions from the control unit 40, to the control unit 40. Various kinds of information stored by the memory unit 30 may be information input by the input unit 20, in-vivo image groups PG input by the image input device 1, results of processing by constituent components of the image processing device 2, and the like, for example.

The control unit 40 controls operations of the computation unit 10, the input unit 20, and the memory unit 30, which constitute the image processing device 2, and controls input/output of signals between these constituent components. In control of the computation unit 10, particularly, the control unit 40 controls operations of the interest area detector 11, the feature amount calculation unit 12, the area classification unit 13, the group feature amount calculation unit 14, the area selection unit 15, and the representative image output unit 16, which constitute the computation unit 10, and controls input/output of signals between these constituent components.

Specifically, the control unit 40 is implemented using the memory unit storing processing programs and a computer executing the processing programs in the memory unit. The control unit 40 controls an operation of the memory unit 30, or controls processes on the constituent components by the computation unit 10 and operation timings of the computation unit 10 and the like, based on instructions from the input unit 20. The control unit 40 also controls the computation unit 10 so as to process the in-vivo image group PG input by the image input device 1 and to output one or more frames of representative images in the in-vivo image group PG, to the display device 3, and controls the memory unit 30 so as to store the in-vivo image group PG. The control unit 40 reads appropriate in-vivo images P(j) in the in-vivo image group PG from the memory unit 30, and transmits the read in-vivo images P(j) to the computation unit 10.

Figure 2:
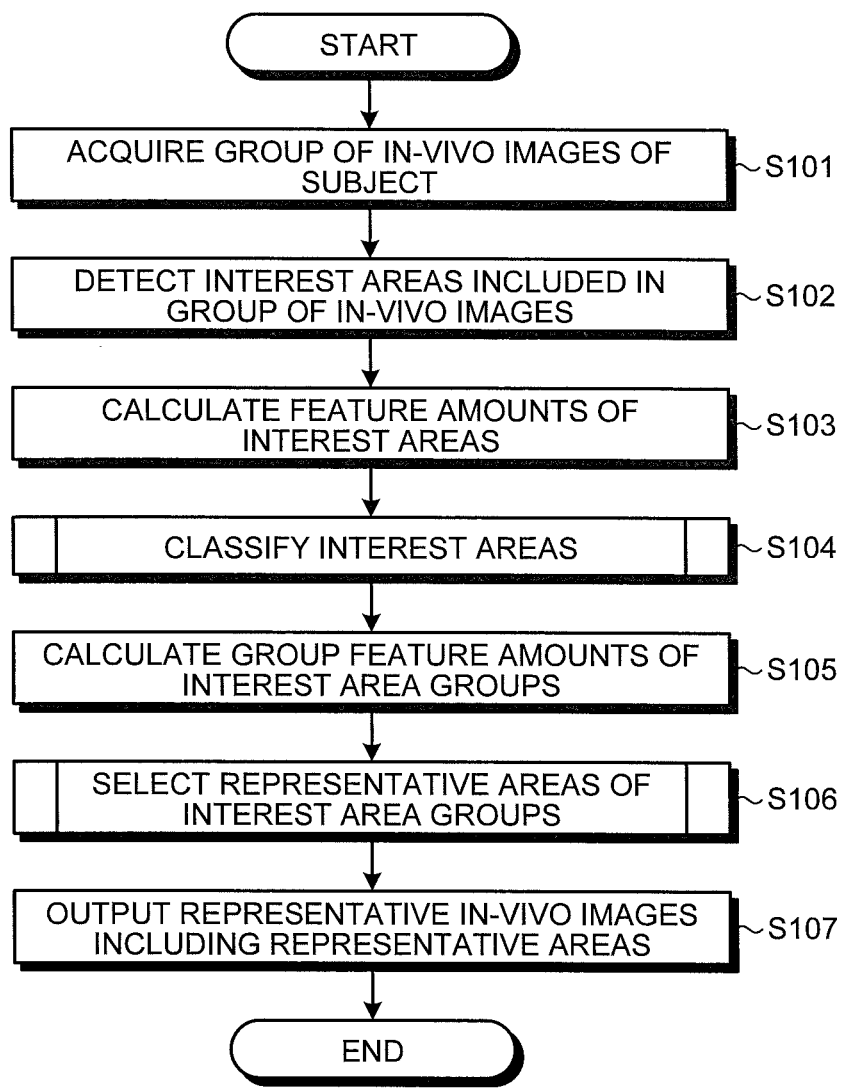
FIG. 2 is a flowchart illustrating one example of a processing procedure of the image processing device according to the first embodiment of the present invention.

Next, an operation of the image processing device 2 in the first embodiment of the present invention will be described below. FIG. 2 is a flowchart of a processing procedure of the image processing device in the first embodiment of the present invention. The image processing device 2 in the first embodiment executes the processing procedure illustrated in FIG. 2, and outputs one or more frames of representative images included in the in-vivo image group PG of a subject acquired from the image input device 1 (hereinafter, referred to as representative in-vivo images), to the display device 3.

Specifically, as illustrated in FIG. 2, the image processing device 2 first acquires the in-vivo image group PG of the subject (step S101). At step S101, the control unit 40 controls the interest area detector 11 of the computation unit 10 so as to execute an acquisition process of the in-vivo image group PG input by the image input device 1. The interest area detector 11 acquires the in-vivo image group PG of the subject from the image input device 1 under the control of the control unit 40, and assigns frame numbers j ($1 \leq j \leq N$) to the in-vivo images P(j) in the acquired in-vivo image group PG (total N images) in time series. The in-vivo images P(j) included in the in-vivo image group PG are color images having pixels with pixel values corresponding to R (red), G (green), and B (blue).

Next, the image processing device 2 detects interest areas A(j, t) included in the in-vivo image group PG (step S102). At step S102, the control unit 40 controls the interest area detector 11 so as to execute a process of detecting the interest areas A(j, t) in the in-vivo image group PG acquired by the foregoing processing procedure at step S101. Under the control of the control unit 40, the interest area detector 11 detects interest areas A(j, t) such as lesion areas, based on color information and the like on the in-vivo images P(j) in the in-vivo image group PG.

Specifically, the interest area detector 11 first divides each of the in-vivo images P(j) in the in-vivo image group PG into a prescribed number of pixel areas, and calculates feature amounts of color or the like of the pixel areas. Then, the interest area detector 11 performs clustering of data points of the pixel areas in a feature space with a coordinate axis of feature amounts of color or the like. After that, the interest area detector 11 identifies clusters constituted by the pixels of the interest areas in the in-vivo images P(j), based on information of positions of barycenters of clusters of data points in the feature space, and sets the pixel areas corresponding to the identified clusters as interest areas A(j, t) in the in-vivo images P(j).

In this arrangement, clustering refers to a process of classifying data distributions in the feature space into groups called clusters, based on similarity in feature amount. In addition, the interest area detector 11 detects the interest areas A(j, t) such as lesion areas included in the in-vivo image group PG, by performing a publicly known clustering method (refer to CG-ARTS Society, "Digital Image Processing", p. 231) such as k-means method, for example.

In the first embodiment, the interest area detector 11 detects the interest areas A(j, t) such as lesion areas based on a distribution state of feature amounts in the feature space, but the method for detecting interest areas A(j, t) by the interest area detector 11 varies depending on the interest areas A(j, t) to be detected. Accordingly, the interest area detector 11 may detect the interest areas A(j, t) in the in-vivo image group PG using any method other than the foregoing clustering, provided that the method allows detection of the interest areas A(j, t) from the in-vivo image group PG.

Subsequently, the image processing device 2 calculates feature amounts of the interest areas A(j, t) included in the in-vivo image group PG (step S103). At step S103, the control unit 40 controls the feature amount calculation unit 12 so as to execute a process of calculating the feature amounts of the interest areas A(j, t) detected by the foregoing processing procedure at step S102. Under the control of the control unit 40, the feature amount calculation unit 12 calculates color feature amounts as an example of feature amounts of the interest areas A(j, t) in the in-vivo image group PG.

Specifically, the pixel value converter 12a converts the values of RGB color space belonging to the interest areas A(j, t) into the values of L*a*b* space, that is, the values of lightness index L and perception chromaticities a and b, for each of the interest areas A(j, t) detected from the in-vivo image group PG by the interest area detector 11. Then, the average calculation unit 12b calculates averages of the values of lightness index L and perception chromaticities a and b converted and output by the pixel value converter 12a for each of the interest areas A(j, t), that is, the average lightness index L(j, t) and the average perception chromaticities a(j, t) and b(j, t), as color feature amounts of the interest areas A(j, t).

As described above, the feature amount calculation unit 12 calculates color feature amounts of the interest areas A(j, t) in a four-axis feature space having coordinate axes of three color feature amounts of lightness index L, perception chromaticities a and b, or the like, and time series (hereinafter, referred to as Lab-time series feature space). In this arrangement, the color feature amounts of the interest areas A(j, t) calculated by the feature amount calculation unit 12 constitute coordinate elements of the color feature axes in the Lab-time series feature space.

In addition, the character j in the foregoing average lightness index L(j, t) and average perception chromaticities a(j, t) and b(j, t), denotes a frame number j assigned to the in-vivo images P(j) in the in-vivo image group PG, as described above. Meanwhile, the character t denotes an index for identifying one or more interest areas A(j, t) included in one frame of in-vivo image P(j) in the in-vivo image group PG.

Next, the image processing device 2 classifies the interest areas A(j, t) in the in-vivo image group PG (step S104). At step S104, the control unit 40 controls the area classification unit 13 so as to execute a process of classifying the interest areas A(j, t) detected by the foregoing processing procedure at step S102. Under the control of the control unit 40, the area classification unit 13 classifies the interest areas A(j, t) in the in-vivo image group PG into area groups, based on the color feature amounts of the interest areas A(j, t) calculated by the processing procedure at step S103 and the time-series positions of the in-vivo images P(j) including the interest areas A(j, t).

Specifically, the adjacent state determination unit 13a determines a time-series adjacent state of the interest areas A(j, t) included in the in-vivo image group PG. Specifically, the adjacent state determination unit 13a determines whether the feature points are adjacent to each other in time series, for each of the interest areas A(j, t) corresponding to the feature points in the Lab-time series feature space. Meanwhile, the degree-of-similarity determination unit 13b determines the degree of similarity in color feature amount between a plurality of interest areas A(j, t) calculated by the average calculation unit 12b at step S103. Specifically, the degree-of-similarity determination unit 13b determines the degree of similarity in the average lightness index L(j, t) and average perception chromaticities a(j, t) and b(j, t) between the feature points in the Lab-time series feature space.

The area classification unit 13 classifies the interest areas A(j, t) in the in-vivo image group PG into one or more area groups, based on the time-series adjacent state of the interest areas A(j, t) determined by the adjacent state determination unit 13a and the degree of similarity in color feature amount between the interest areas A(j, t) determined by the degree-of-similarity determination unit 13b. Accordingly, the area classification unit 13 classifies the feature points distributed in the Lab-time series feature space into one or more feature point clusters.

The feature points in the Lab-time series feature space are coordinate points defined by the color feature amounts and time-series positions of the interest areas A(j, t). Meanwhile, the feature point clusters refer to groups of feature points distributed in the Lab-time series feature space, including one or more feature points. At step S104, the area classification unit 13 regards a group including a plurality of feature points as a feature point cluster in the Lab-time series feature space, and also regards a single feature point as a feature point cluster to which the one feature point belongs in the Lab-time series feature space.

Subsequently, the image processing device 2 calculates group feature amounts of the interest area groups in the in-vivo image group PG (step S105). At step S105, the control unit 40 controls the group feature amount calculation unit 14 so as to execute a process of calculating group feature amounts of the area groups of the interest areas A(j, t) classified by the foregoing processing procedure at step S104.

Specifically, under the control of the control unit 40, the group feature amount calculation unit 14 calculates group feature amounts indicating features of the area groups of the interest areas A(j, t). That is, the group feature amount calculation unit 14 first calculates dispersion of color feature amounts of the interest areas A(j, t) included in the in-vivo image group PG. Then, the group feature amount calculation unit 14 totalizes the color feature amounts of the interest areas A(j, t) belonging to each of the area groups, thereby to calculate group feature amounts of the area groups in the in-vivo image group PG.

More specifically, the group feature amount calculation unit 14 calculates dispersion of average lightness index L(j, t) and average perception chromaticities a(j, t) and b(j, t) of the feature points in the Lab-time series feature space, and then totalizes dispersion of the calculated average lightness index L(j, t) and average perception chromaticities a(j, t) and b(j, t) for each of the feature point clusters. Accordingly, the group feature amount calculation unit 14 calculates a group feature amount of each of the feature point clusters in the in-vivo image group PG, that is, a group feature amount of each of the area groups.

Next, the image processing device 2 selects representative areas of the interest area groups in the in-vivo image group PG (step S106). At step S106, the control unit 40 controls the area selection unit 15 so as to execute a process of selecting representative areas from each of the area groups of the interest areas A(j, t) classified by the foregoing processing procedure at step S104.

Specifically, under the control of the control unit 40, the area selection unit 15 selects one or more representative areas from the interest areas A(j, t) belonging to each of the area groups, based on the group feature amounts of the area groups calculated by the foregoing group feature amount calculation unit 14.

After that, the image processing device 2 outputs one or more frames of representative in-vivo images including the representative areas in the in-vivo image group PG, to the display device 3 (step S107), thereby terminating this process. At step S107, the control unit 40 controls the representative image output unit 16 so as to execute a process of outputting the representative in-vivo images including the representative areas selected by the foregoing processing procedure at step S106.

Specifically, under the control of the control unit 40, the representative image output unit 16 extracts from the in-vivo image group PG, one or more frames of representative in-vivo images including the representative areas selected by the area selection unit 15 at foregoing step S106, and outputs the extracted one or more frames of representative in-vivo images to the display device 3. That is, if only one frame of representative in-vivo image is included in the in-vivo image group PG, the representative image output unit 16 outputs the one frame of representative in-vivo image to the display device 3. If a plurality of frames of representative in-vivo images is included in the in-vivo image group PG, the representative image output unit 16 outputs the plurality of frames representative in-vivo images to the display device 3. In addition, the representative in-vivo images output by the representative image output unit 16 to the display device 3 may include a single interest area A(j, 1) or include a plurality of interest areas A(j, t) (t≥2).

Figure 3:
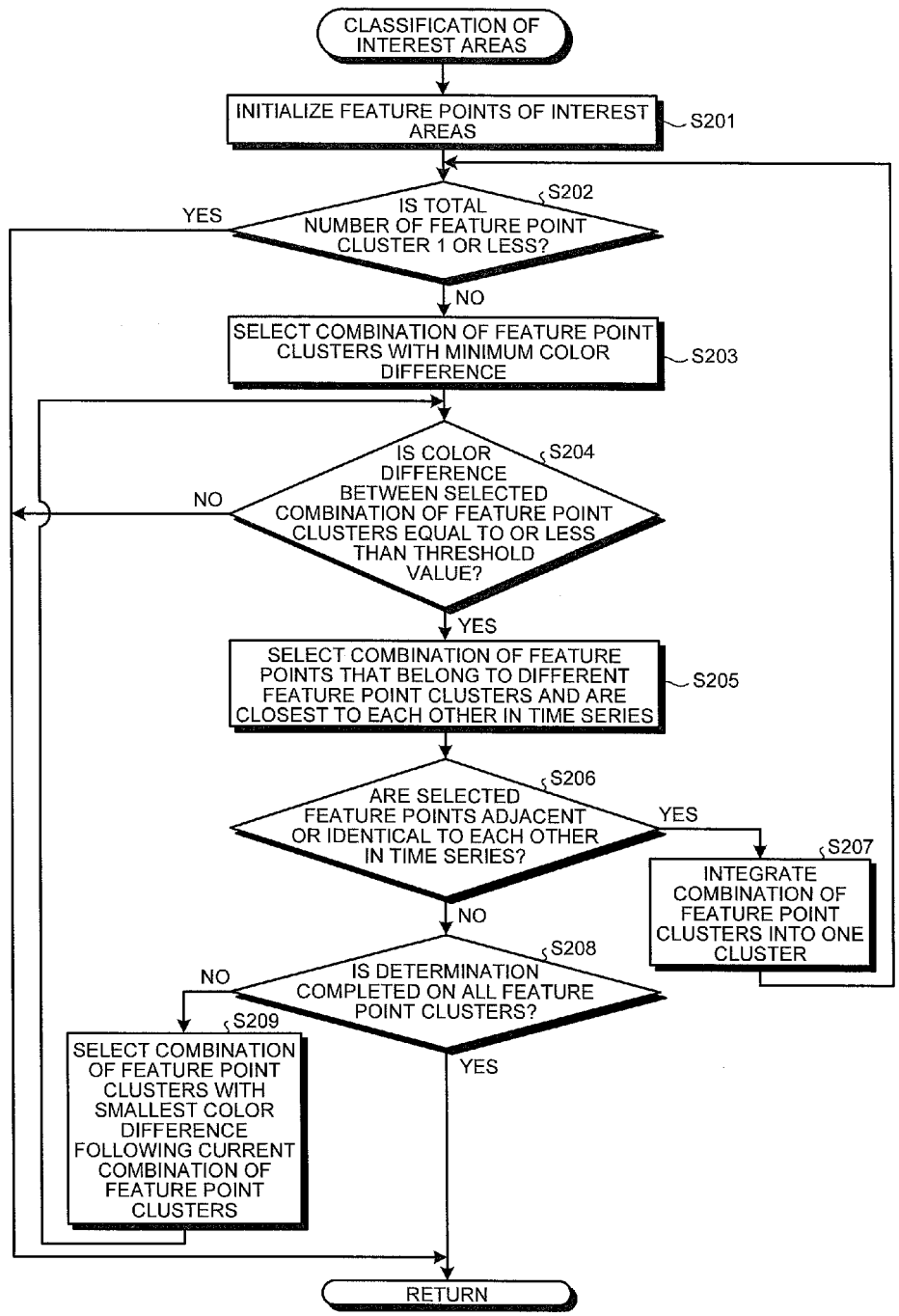
FIG. 3 is a flowchart illustrating one example of a processing procedure of classifying interest areas included in an in-vivo image group.
Figure 4:
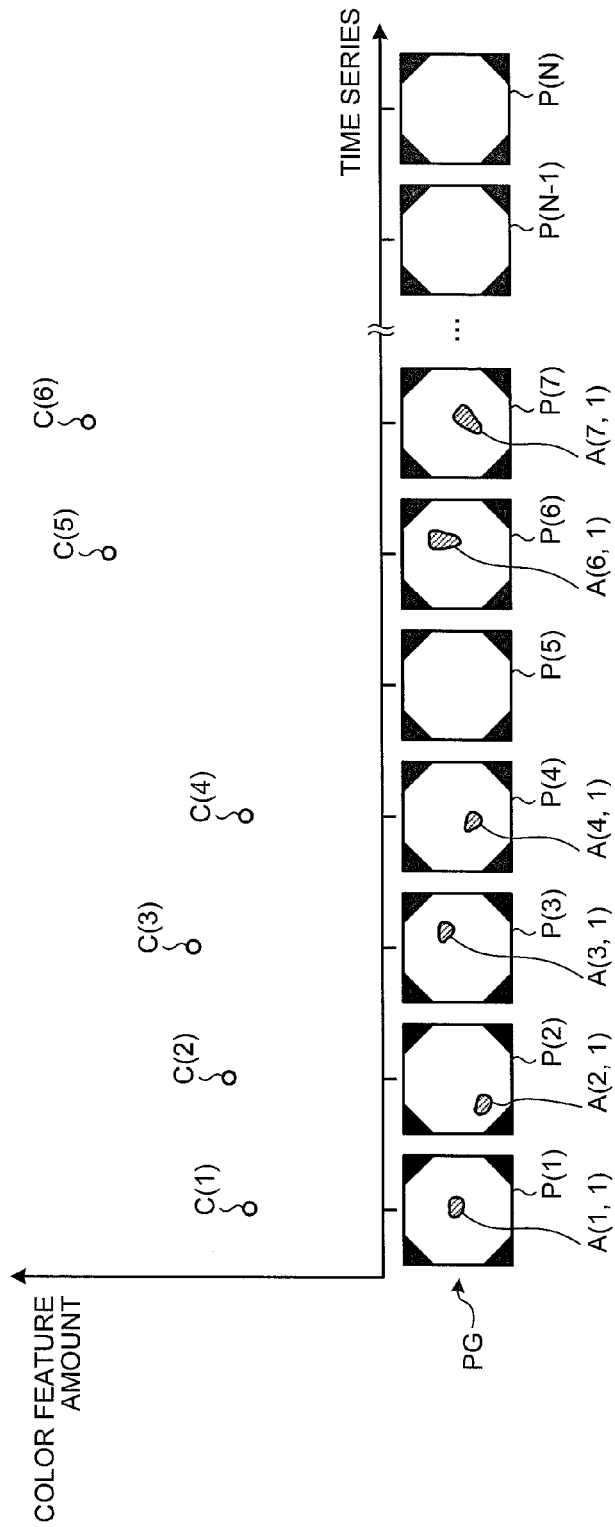
FIG. 4 is a schematic diagram illustrating a specific example of a distribution state of feature points of the interest areas included in the in-vivo image group in a feature space.
Figure 5:
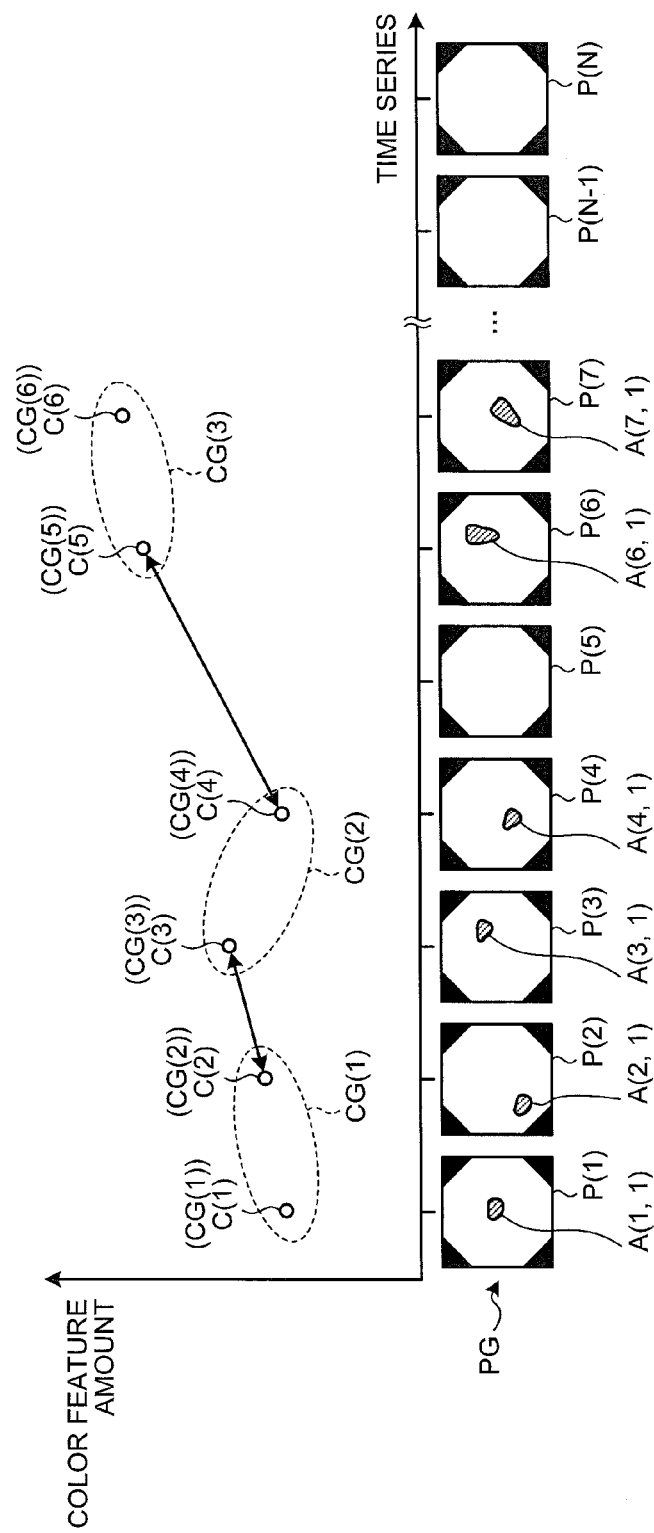
FIG. 5 is a schematic diagram illustrating that the feature points in the feature space are classified into feature point clusters.
Figure 6:
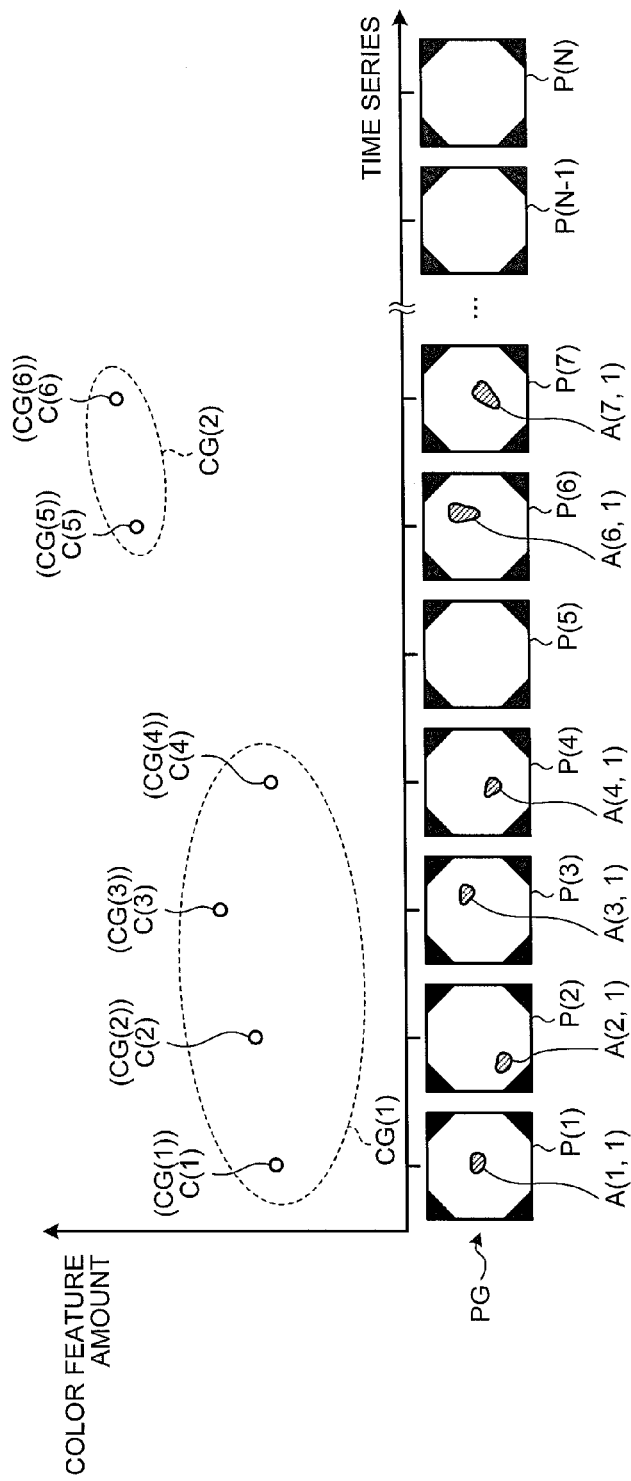
FIG. 6 is a schematic diagram illustrating that a plurality of feature point clusters to which time-series adjacent or identical feature points belong, are integrated into one cluster.

Next, the process of classifying the interest areas at foregoing step S104 will be described in detail. FIG. 3 is a flowchart of an example of a process of classifying the interest areas included in an in-vivo image group. FIG. 4 is a schematic diagram illustrating a specific example of a distribution state of feature points of interest areas included in the in-vivo image group in a feature space. FIG. 5 is a schematic diagram illustrating a state of classifying feature points in the feature space into feature point clusters. FIG. 6 is a schematic diagram illustrating a state of integrating a plurality of feature point clusters in which feature points are adjacent or identical to each other in time series into one and the same cluster.

The feature space illustrated in FIGS. 4 to 6 is a Lab-time series feature space. In FIGS. 4 to 6, the average lightness index L(j, t) and the average perception chromaticities a(j, t) and b(j, t) are expressed collectively in one axis as color feature amounts.

The area classification unit 13 of the image processing device 2 executes the process of classifying the interest areas A(j, t) at step S104 under the control of the control unit 40, as described above. Specifically, as illustrated in FIG. 3, the area classification unit 13 first initializes feature points of the interest areas A(j, t) included in the in-vivo image group PG (step S201).

At step S201, the area classification unit 13 creates (plots) feature points corresponding to features of the interest areas A(j, t) in the in-vivo image group PG, based on the color feature amounts of the interest areas A(j, t) calculated by the forgoing feature amount calculation unit 12 and the time-series positions of the in-vivo images P(j) including the interest areas A(j, t).

Specifically, if the total number Tm of interest areas A(j, t) are included in the in-vivo images P(j) of the in-vivo image group PG, the area classification unit 13 plots feature points C(m) of the interest areas A(j, t) in the Lab-time series feature space, based on time-series information and color feature amounts of the interest areas A(j, t). The character m in the feature points C(m) denotes an index for identifying feature points plotted in the Lab-time series feature space. That is, the index m is larger than 1 and smaller than Tm in the total number Tm of interest areas A(j, t). Meanwhile, the time-series information of the interest areas A(j, t) is information indicative of time-series positions of the in-vivo images P(j) in the in-vivo image group PG, which corresponds to the frame number j for the in-vivo images P(j). In addition, the color feature amounts of the interest areas A(j, t) are the average lightness index L(j, t) and the average perception chromaticities a(j, t) and b(j, t) calculated by the average calculation unit 12b.

In this arrangement, the area classification unit 13 first sets the index m as "1", and sets coordinates of a feature point C(1) based on the color feature amounts and time-series information of the feature point C(1), thereby creating the feature point C(1) in the Lab-time series feature space. Subsequently, as for remaining feature points C(2) to C(Tm), the area classification unit 13 creates the feature points C(2) to C(Tm) in the Lab-time series feature space by setting coordinates in sequence based on the color feature amounts and time-series information as in the case of the feature point C(1). At this point of time, the area classification unit 13 regards the feature points C(1) to C(Tm) distributed in the Lab-time series feature space as individual feature point clusters, thereby to create a set of the same number of feature point cluster as that of the detected interest area A(j, t).

Next, the area classification unit 13 sets the total number of the created feature point clusters as Tk, and sets index k (1≤k≤Tk) for identifying feature point clusters CG(k) in the feature point cluster set as "1". Then, the area classification unit 13 assigns the color feature amounts of the interest areas A(j, t) constituting the feature point clusters CG(k), that is, the average lightness index L(j, t) and the average perception chromaticities a(j, t) and b(j, t), into average lightness index L(k) and average perception chromaticities a(k) and b(k) of the feature point cluster CG(k) (a process of assigning the color feature amounts).

In this arrangement, the average lightness index L(k) and the average perception chromaticities a(k) and b(k) constitute averages of the color feature amounts of all the interest areas A(j, t) belonging to the feature point clusters CG(k). At this stage, however, each of the feature point clusters CG(k) includes only one interest area A(j, t), that is, one feature point C(m). For this reason, the area classification unit 13 assigns the lightness index L(j, t) and the perception chromaticities a(j, t) and b(j, t) of the interest areas A(j, t) belonging to the feature point clusters CG(k), into the average lightness index L(k) and the average perception chromaticities a(k) and b(k).

After that, the area classification unit 13 increments the index k and determines whether the index k is equal to or less than the total number Tk. If determining that the index k is equal to or less than the total number Tk, the area classification unit 13 repeatedly performs the processing procedures subsequent from the foregoing process of assigning the color feature amounts. If determining that the index k is not less than the total number Tk, the area classification unit 13 terminates the process procedure at step S201.

Referring to FIG. 4, the processing procedure at step S201 will be described below in more detail. As illustrated in FIG. 4, if in-vivo images P(1), P(2), P(3), P(4), P(6), and P(7) in the in-vivo image group PG includes interest areas A(1, 1), A(2, 1), A(3, 1), A(4, 1), A(6, 1), and A(7, 1), respectively, the area classification unit 13 first creates the feature point C(1) having coordinates based on time-series information and color feature amounts of the interest area A(1, 1) in the in-vivo image P(1), in the Lab-time series feature space. Then, the area classification unit 13 creates sequentially the feature point C(2) having coordinates based on time-series information and color feature amounts of the interest area A(2, 1) in the in-vivo image P(2) to the feature point C(6) having coordinates based on time-series information and color feature amounts of the interest area A(7, 1) in the in-vivo image P(7), in the Lab-time series feature space. As a result, the six feature points C(1) to C(6), which are the same number as the total number Tm (=6) of the interest areas, are plotted in the Lab-time series feature space as illustrated in FIG. 4.

Next, the area classification unit 13 regards the six feature points C(1) to C(6) as individual feature point clusters, and assigns the color feature amounts of the feature points C(1) to C(6) into the color feature amounts of the feature point clusters, that is, the average lightness index L(k) and the average perception chromaticities a(k) and b(k).

Since the in-vivo image P(5) in the in-vivo image group PG does not include any interest area, no feature point is plotted corresponding to the in-vivo image P(5) in the Lab-time series feature space. This also applies to the remaining in-vivo images P(8) to P(N).

Meanwhile, after executing foregoing step S201, the area classification unit 13 determines whether the total number of feature point clusters in the Lab-time series feature space is equal to or less than 1 (step S202). At step S202, the area classification unit 13 counts the number of feature point clusters existing in the Lab-time series feature space, and determines whether the total number of the counted feature point clusters is equal to or less than 1.

If the total number of feature point clusters is found to be equal to or less than 1 as a result of the determination process at step S202 (step S202, Yes), the area classification unit 13 terminates this process and returns to the process procedure at step S104 illustrated in FIG. 2. Meanwhile, if the total number of feature point clusters is not found to be equal to or less than 1 as a result of the determination process at step S202 (step S202, No), the area classification unit 13 selects a combination of feature point clusters with a minimum color difference from a plurality of feature point clusters existing in the Lab-time series feature space (step S203).

At step S203, the area classification unit 13 extracts sequentially the feature point clusters CG(k1) and CG(k2) with different indexes k1 and k2 (1≤k1<k2≤Tk) from the plurality of feature point clusters CG(k) set in the Lab-time series feature space, as in the foregoing process procedure at step S201, and then calculates sequentially a color difference ΔE as a difference in color feature amount between the two extracted feature point clusters CG(k1) and CG(k2), in accordance with following Equation (1):

$$\Delta E = \sqrt{(L(k1) - L(k2))^2 + (a(k1) - a(k2))^2 + (b(k1) - b(k2))^2} \quad (1)$$

In Equation (1), the average lightness index L(k1) and the average perception chromaticities a(k1) and b(k1) are color feature amounts of the feature point cluster CG(k1), and the average lightness index L(k2) and the average perception chromaticities a(k2) and b(k2) are color feature amounts of the feature point cluster CG(k2).

Specifically, the area classification unit 13 first sets an initial value of the index k1 at "1," sets an initial value of the index k2 at "2," and then calculates a color difference ΔE between the feature point clusters CG(k1) and CG(k2) in accordance with Equation (1). Then, the area classification unit 13 determines whether the index k2 is less than the total number Tk of feature point clusters. If the index k2 is less than the total number Tk, the area classification unit 13 repeats sequentially the foregoing processes of calculating the color difference ΔE and incrementing the index k2.

After that, if the index k2 is equal to or more than the total number Tk of feature point clusters, the area classification unit 13 determines whether the index k1 is less than a subtracted value in which "1" is subtracted from the total number Tk of feature point clusters (Tk−1). If the index k1 is less than the subtracted value (Tk−1), the area classification unit 13 increments the index k1, sets the index k2 at a value in which "1" is added to the index k1 (k1+1), and repeatedly performs the foregoing process of calculating the color difference ΔE.

Meanwhile, if the index k1 is equal to or more than the subtracted value (Tk−1), the area classification unit 13 sorts all the color differences ΔE calculated at step S203. Based on results of the sorting process, the area classification unit 13 selects a combination of feature point clusters CG(k1) and CG(k2) with a minimum color difference ΔEmin out of all the color differences ΔE.

The color difference ΔE is equivalent to the degree of similarity in color feature amount between the interest areas A(j, t), and decreases with increase in the degree of similarity in color feature amount between the interest area A(j, t) and increases with decrease in the degree of similarity in feature amount between the interest areas A(j, t).

Referring to FIG. 4, the process procedure at step S202 will be described below in more detail. As illustrated in FIG. 4, in the case of an initial state where only one feature point belongs to one feature point cluster, the area classification unit 13 first sets the index k1 of the feature point cluster CG(k1) at the index (=1) of the feature point C(1), and sets the index k2 of the feature point cluster CG(k2) at the index (=2) of the feature point C(2).

Next, the area classification unit 13 calculates a color difference ΔE between the feature point C(1) belonging to the feature point cluster CG(k1) and the feature point C(2) belonging to the feature point cluster CG(k2). Subsequently, the area classification unit 13 determines whether the index k2 is equal to or less than the total number Tk of the feature point clusters. If the index k2 is equal to or less than the total number Tk, the area classification unit 13 increments the index k2 and calculates a color difference ΔE between the feature point C(1) and the feature point C(3) belonging to the feature point cluster CG(k2). After that, the area classification unit 13 repeats sequentially the processes of incrementing the index k2 and calculating the color difference ΔE until the index k2 reaches the total number Tk.

Meanwhile, if the index k2 exceeds the total number Tk, the area classification unit 13 increments the index k1, and substitutes the value of k1+1 for the index k2. Then, the area classification unit 13 calculates a color difference ΔE between the feature point C(2) belonging to the feature point cluster CG(k1) after the increment process and the feature pint C(3) belonging to the feature point cluster CG(k2). After that, the area classification unit 13 repeats sequentially the processes of incrementing the indexes k1 and k2 and calculating the color difference ΔE until the index k1 reaches the value obtained by subtracting "1" from the total number Tk.

After that, the area classification unit 13 executes the foregoing processes on all the combinations of two feature point cluster CG(k1) and CG(k2) extractable from the Lab-time series feature space, thereby to calculate the color differences ΔE between all the combinations of the two feature point clusters CG(k1) and CG(k2).

In such a manner as described above, for the feature points C(1) to C(6) as six feature point clusters in the Lab-time series feature space illustrated in FIG. 4, the area classification unit 13 calculates sequentially the color difference ΔE1 between the feature points C(1) and C(2), the color difference ΔE2 between the feature points C(1) and C(3), the color difference ΔE3 between the feature points C(1) and C(4), the color difference ΔE4 between the feature pints C(1) and C(5), and the color difference ΔE5 between the feature points C(1) and C(6). Then, the area classification unit 13 calculates sequentially the color difference ΔE6 between the feature points C(2) and C(3), the color difference ΔE7 between the feature points C(2) and C(4), the color difference ΔE8 between the feature points C(2) and C(5), and the color difference ΔE9 between the feature points C(2) and C(6). In addition, the area classification unit 13 calculates sequentially the color difference ΔE10 between the feature points C(3) and C(4), the color difference ΔE11 between the feature points C(3) and C(5), and the color difference ΔE12 between the feature points C(3) and C(6). Further, the area classification unit 13 calculates sequentially the color difference ΔE13 between the feature points C(4) and C(5), the color difference ΔE14 between the feature points C(4) and C(6), and then the color difference ΔE15 between the feature points C(5) and C(6)

After calculating the color differences ΔE between all the combinations of feature point clusters CG(k1) and CG(k2) as described above, the area classification unit 13 compares all the calculated color differences ΔE, and sorts all the color differences ΔE. Then, the area classification unit 13 determines a minimum color difference ΔEmin from all the color difference ΔE, based on results of the sort process. In addition, from all the combinations of feature point clusters in the Lab-time series feature space, the area classification unit 13 selects a combination of feature point clusters CG(k1) and CG(k2) corresponding to the minimum color difference ΔEmin.

Specifically, if the color difference ΔE3 between the feature points C(1) and C(4) has a minimum value as illustrated in FIG. 4, the area classification unit 13 determines the color difference ΔE3 as minimum color difference ΔEmin from all the calculated color differences ΔE1 to ΔE15. In addition, the area classification unit 13 selects a combination of feature point clusters corresponding to the color difference ΔE3, that is, the feature points C(1) and C(4), from all the combinations of feature points C(1) to C(6) as feature point clusters.

Meanwhile, after executing step S203, the area classification unit 13 determines whether the color difference ΔE between the selected combination of feature point clusters CG(k1) and CG(k2) is equal to or less than a prescribed threshold value (step S204).

At step S204 immediately after forgoing step S203, the area classification unit 13 compares the minimum color difference ΔEmin between the feature point clusters to which only one feature point belongs with the threshold value for color feature amounts in the Lab-time series feature space. At step S204 immediately after step S209 described later, the area classification unit 13 compares the minimum color difference ΔEmin in the combination of feature point clusters selected in the process procedure at step S209 with the threshold value. If the minimum color difference ΔEmin is not equal to or less than the threshold value (step S204, No), the area classification unit 13 terminates this process and returns to the process procedure at step S104 illustrated in FIG. 2.

The foregoing threshold value of the color difference ΔEmin is set in accordance with a unit system of color difference ΔE, for example, an NBS (National Bureau of Standards) unit system in which a range of values corresponding to color differences sensed by humans is determined, for example. Specifically, the threshold value is desirably set at a value with which color differences can be recognized by humans (=3.0). The threshold value may be held in advance at the area classification unit 13 or may be set so as to be capable of updated by the control unit 40 based on information input from the input unit 20.

Meanwhile, if determining at step S204 that the color difference between the combination of feature point clusters, that is, the minimum color difference ΔEmin is equal to or less than the threshold value (step S204, Yes), the area classification unit 13 selects a combination of feature points which belong to different feature point clusters in the Lab-time series feature space closest to each other in time series, from the combinations of feature point clusters (step S205).

At step S205, from the combinations of feature point clusters with the minimum color difference ΔEmin determined as being equal to or less than the threshold value in the process procedure at step S204, the area classification unit 13 first sets a feature point C(t1) belonging to one of the feature point clusters and a feature point C(t2) belonging to the other feature point cluster.

In this arrangement, t1 denotes an index for identifying the feature point belonging to the one feature point cluster, and is also an index for identifying the interest areas in the area group corresponding to the one feature point cluster. Similarly, t2 denotes an index for identifying the feature point belonging to the other feature point cluster, and is also an index for identifying the interest areas in the area group corresponding to the other feature point cluster.

The area classification unit 13 sets a numerical range of index t1 for the feature point belonging to the one feature point cluster ($1 \leq t1 \leq Q1$), and a numerical range of index t2 for the feature point belonging to the other feature point cluster ($1 \leq t2 \leq Q2$). In addition, Q1 denotes a maximum value of index t1 which shows the total number of interest areas corresponding to the one feature point cluster. Meanwhile, Q2 denotes a maximum value of index t2 which shows the total number of interest areas corresponding to the other feature point cluster.

In this arrangement, the area classification unit 13 regards a group including a plurality of feature point as a feature point clusters in the Lab-time series feature space, and also regards a single feature point as a feature point cluster to which the one feature point belongs in the Lab-time series feature space.

The interest areas corresponding to the foregoing feature points are equivalent to the interest areas A(j, t) such as lesion areas detected by the interest area detector 11 at step S102 illustrated in FIG. 2, and are equivalent to the interest areas A(1, 1), A(2, 1), A(3, 1), A(4, 1), A(6, 1), and A(7, 1) illustrated in FIG. 4.

Subsequently, the area classification unit 13 calculates a distance D in a time-series direction between the interest area identified by the index t1 and the interest area identified by the index t2. Specifically, the area classification unit 13 first sets both of the indexes t1 and t2 at "1," and then calculates an Euclidean distance, as distance D, in a time-series direction between the feature point C(1) in one feature point cluster corresponding to the interest area with the index t1=1 and the feature point C(t2) in the other feature point cluster corresponding to the interest area with the index t2=1.

Next, the area classification unit 13 determines whether the index t1 is less than the total number Q1. If the index t1 is less than the total number Q1, the area classification unit 13 increments the index t1, and calculates the distance D in the time-series direction between the interest area identified by the index t1 and the interest area identified by the index t2 after the increment process. After that, the area classification unit 13 repeats sequentially the processes of incrementing the index t1 and calculating the distance D until the index t1 reaches the total number Q1.

Meanwhile, if the index t1 is equal to or more than the total number Q1, the area classification unit 13 determines whether the index t2 for the feature point belonging to the other feature point cluster is less than the total number Q2. If the index t2 is less than the total number Q2, the area classification unit 13 sets the index t1 at an initial value (=1), increments the index t2, and then calculates the distance D in the time-series direction between the interest area identified by the index t2 and the interest area identified by the index t1. After that, the area classification unit 13 repeats sequentially the processes of incrementing the index t2 and calculating the distance D until the index t2 reaches the total Q2.

As described above, by repeatedly performing the processes of incrementing the indexes t1 and t2 and calculating the distance D, the area classification unit 13 completes the calculation of the distance in the time-series direction between the feature point C(t1) belonging to the one feature point cluster and the feature point C(t2) belonging to the other feature point cluster, that is, the distance D in the time-series direction between the interest areas in the two feature point clusters. After that, the area classification unit 13 sorts all the calculated distances D, and determines a minimum distance Dmin out of all the distances D, based on results of the sort process.

In this arrangement, the combination of feature points corresponding to the distance Dmin is a combination of feature points closest to each other in time series in the Lab-time series feature space. That is, the area classification unit 13 selects the combination of feature points corresponding to the distance Dmin as a combination of feature points which belong to different feature point clusters and are closest to each other in time series in the Lab-time series feature space. By performing this process of selecting the combination of feature points, the area classification unit 13 selects the combination of interest areas which belong to different feature point clusters and are closest to each other in time series.

Meanwhile, after executing foregoing step S205, the area classification unit 13 determines whether the feature points in the combination selected in the process procedure at step S205 are adjacent or identical to each other in time series (step S206).

At step S206, based on the time-series distance D between the feature points in the combination selected by the process procedure at step S205, the adjacent state determination unit 13a determines a time-series adjacent state of the interest areas corresponding to the feature points in the combination selected in the process procedure at step S205. That is, the adjacent state determination unit 13a determines whether the feature points in the selected combination are adjacent or identical to each other in time series, based on the time-series distance D.

If the adjacent state determination unit 13a determines at step S206 that the feature points in the combination are adjacent or identical to each other (step S206, Yes), the area classification unit 13 integrates the combination of the feature point clusters to which the feature points adjacent or identical to each other in time series belong, into one cluster (step S207).

Specifically, at step S207, out of the indexes k1 and k2 for two feature point clusters CG(k1) and CG(k2) to which the two combined feature points adjacent or identical to each other in time series belong, the area classification unit 13 first sets the smaller one as a minimum index ka and sets the larger one as a maximum index kb.

Next, the area classification unit 13 sets the minimum index ka as a new index for identifying the feature point cluster after the integration process, and creates a new feature point cluster CG(ka) into which all the feature points in the two feature point clusters to which the two feature points adjacent or identical to each other in time series belong, are integrated.

After that, the area classification unit 13 calculates an average lightness index L(ka) and average perception chromaticities a(ka) and b(ka) as color feature amounts of the feature point cluster CG(ka), based on the color feature amounts of the feature points belonging to the feature point cluster CG(ka). Specifically, the area classification unit 13 calculates an average of lightness indexes of the feature points in the feature point cluster CG(k) as average lightness index L(ka), and calculates an average of perception chromaticities of the feature points as average perception chromaticities a(ka) and b(ka).

At this point of time, the feature point cluster identified by the maximum index kb is integrated into the new feature point cluster CG(ka) and therefore does not exist. In this state, out of all the feature point clusters existing in the Lab-time series feature space, the area classification unit 13 decrements the indexes k for the remaining feature point clusters identified by indexes larger than the maximum index kb.

Specifically, the area classification unit 13 first assigns the maximum index kb to a tentative index ki. Then, the area classification unit 13 determines whether the index ki (=kb) after the assignment process is less than the total number Tk of the feature point clusters. If the index ki is less than the total number Tk, the area classification unit 13 increments the index ki. Next, the area classification unit 13 decrements the index of the feature point cluster CG(k) (change to k−1) shown by the index ki after the increment process (=kb+1). After that, the area classification unit 13 repeats the processes of incrementing the index ki and decrementing the index k until the index ki becomes equal to or more than the total number Tk. Meanwhile, if the index ki is not less than the total number Tk, the area classification unit 13 terminates the foregoing processes of incrementing the index ki and decrementing the index k.

In this arrangement, the total number Tk of feature point clusters at this point of time in the Lab-time series feature space is decreased by one in the foregoing process of integrating the feature point clusters. Accordingly, if the index ki is not less than the total number Tk, the area classification unit 13 subtracts "1" from the total number Tk before the process of integrating the feature point clusters, and updates the total number Tk after the subtraction process to the total number of feature point clusters at this point of time in the Lab-time series feature space.

After completion of the process procedure at step S207, the area classification unit 13 returns to foregoing step S202 and repeats the process procedures at step S202 and later. Meanwhile, if determining that the feature points in the combination are not adjacent or equal to each other in time series by the adjacent state determination unit 13a at foregoing step S206 (step S206, No), the area classification unit 13 determines whether the process of determining the time-series state is completely performed on all the combinations of the feature point clusters in the Lab-time series feature space (step S208).

At step S208, the area classification unit 13 determines whether the process of determining the time-series state is completely performed on all the combinations of feature point clusters, based on the indexes or the like of feature point clusters having been subjected to the process of determining the time-series state at step S206. If determining that the process of determining the time-series state is completely performed on all the combinations of feature point clusters (step S208, Yes), the area classification unit 13 terminates this process and returns to the process procedure at step S104 illustrated in FIG. 2.

Meanwhile, if determining that the process of determining the time-series state is not completely performed on all the combinations of feature point clusters at step S208 (step S208, No), the area classification unit 13 selects the combination of feature point clusters with a smallest color difference ΔE following that of the current combination of feature point clusters selected at foregoing step S205 (step S209). After that, the area classification unit 13 returns to foregoing step S204, and repeats the process procedures at step S204 and later.

At step S209, from all the color differences ΔE calculated by the process procedure at foregoing step S203, the area classification unit 13 selects the color difference ΔE smallest following the color difference ΔE (the current minimum color difference ΔEmin) of the current combination of feature point clusters, as minimum color difference ΔEmin. Then, from all the feature point clusters in the Lab-time series feature space, the area classification unit 13 selects the combination of feature point clusters having the selected minimum color difference ΔEmin.

In this arrangement, by repeatedly performing the process procedures at foregoing steps S201 to S209, the area classification unit 13 classifies all the feature points in the Lab-time series feature space into feature point clusters based on time-series information and color feature amount information. Accordingly, the area classification unit 13 classifies all the interest areas A(j, t) detected from the in-vivo image group PG by the interest area detector 11, into area groups corresponding to the feature point clusters. Specifically, the area classification unit 13 classifies the interest areas A(j, t) into area groups based on color feature amounts of the interest areas A(j, t) calculated by the feature amount calculation unit 12 and time-series positions of the in-vivo images P(j) including the interest areas A(j, t).

Meanwhile, after the area classification unit 13 executes repeatedly the process procedures at foregoing steps S201 to S209, the group feature amount calculation unit 14 calculates group feature amounts for the area groups of the interest areas A(j, t) at step S105 illustrated in FIG. 2, as described above.

Specifically, the group feature amount calculation unit 14 calculates barycenters L(k), a(k), and b(k) of each of the feature point clusters in the Lab-time series feature space. Then, the group feature amount calculation unit 14 uses the calculated barycenters L(k), a(k), and b(k) of the feature point clusters to calculate dispersion of average lightness index L(j, t) and average perception chromaticities a(j, t) and b(j, t) as color feature amounts of the interest areas A(j, t) belonging to the same feature point cluster, for each of the feature point clusters. The group feature amount calculation unit 14 calculates a sum total Sum(k) of dispersion of the average lightness index L(j, t) and average perception chromaticities a(j, t) and b(j, t) in the same feature point cluster, for each of the feature point clusters, in accordance with Equation (2) shown below. The sum total Sum(k) thus calculated by the group feature amount calculation unit 14 is a group feature amount of each of the area groups of the interest areas A(j, t).

$$\mathrm{Sum}(k) = \frac{1}{\mathrm{Num}(k)} \sum_{j(k)\min}^{j(k)\max} \sum_{t=1}^{\mathrm{Num}(t)} ((L(j,t) - L(k))^2 + (a(j,t) - a(k))^2 + (b(j,t) - b(k))^2) \quad (2)$$

In Equation (2), the Num(k) denotes the total number of feature points belonging to the feature point cluster CG(k), that is, the total number of the interest areas A(j, t); j(k) max denotes the maximum value of index j of the interest areas A(j, t) belonging to the feature point cluster CG(k); and Num(t) denotes, out of the interest areas A(j, t) detected from the in-vivo images P(j) in the in-vivo image group PG, the number of interest areas belonging to the feature point cluster CG(k).

Meanwhile, the barycenters L(k), a(k), and b(k) refer to coordinate points in the Lab-time series feature space, which have the average of time-series positions and the average of color feature amounts in the same feature point cluster as coordinate elements. Out of the same, the barycenter L(k) corresponds to the average lightness index L(j, t) out of the color feature amounts of the interest areas A(j, t), and the barycenter a(k) corresponds to the average perception chromaticity a(j, t) out of the color feature amounts of the interest areas A(j, t), and the barycenter b(k) corresponds to the average perception chromaticity b(j, t) out of the color feature amounts of the interest areas A(j, t).

Referring to FIGS. 5 and 6, the process procedures at steps S202 to S209 executed by the area classification unit 13 will be described in detail. As illustrated in FIG. 5, if the total number Tm=6 of the feature points C(1) to C(6) exist in the Lab-time series feature space, the area classification unit 13 performs sequentially the process procedures at foregoing steps S202 and S203, regarding the six feature points C(1) to C(6) as feature point clusters (CG(1) to (CG(6)), and then calculates sequentially color differences ΔE1 to ΔE15 between all the combinations of two feature point clusters selectable from the six feature point clusters (CG(1) to CG(6)).

Then, the area classification unit 13 compares the calculated color differences ΔE1 to ΔE15, and, based on results of the comparison process, decides the color difference ΔE3 which is smallest among all the color differences ΔE1 to ΔE15, as minimum color difference ΔEmin. In FIG. 5, from all the combinations of feature point clusters, the area classification unit 13 selects the combination of feature point clusters (CG(1)) and (CG(4)) corresponding to the color difference ΔE3.

Next, the area classification unit 13 performs sequentially foregoing steps S204 and S205, and selects the combination of feature point clusters (CG(1)) and (CG(4)) corresponding to the color difference ΔE3 which is equal to or less than a prescribed threshold value. Then, the area classification unit 13 performs the process procedure at foregoing step S206, and determines whether the feature point C(1) and feature point C(4) in the selected combination are adjacent or identical to each other in time series.

In this arrangement, the feature point C(1) and feature point C(4) are not adjacent or identical to each other in time series as illustrated in FIG. 5. Accordingly, the area classification unit 13 executes the process procedure at foregoing step S208, and then executes foregoing step S209 because the process of determining the time-series state is not completely performed on the feature point clusters. In FIG. 5, the area classification unit 13 selects the combination of feature point clusters having the smallest color difference following the color difference ΔE3 of the current combination of feature point clusters (CG(1)) and (CG(4)), for example, the combination of feature point clusters (CG(1)) and (CG(2)).

Subsequently, the area classification unit 13 executes again foregoing steps S204 and S205 to select the feature points C(1) and C(2) which belong to different feature point clusters and are closest to each other in time series. Then, the area classification unit 13 executes again foregoing step S206 to determine whether the selected feature point C(1) and feature point C(2) are adjacent or identical to each other in time series.

In this arrangement, the feature point C(1) and feature point C(2) are adjacent to each other in time series as illustrated in FIG. 5. Accordingly, the area classification unit 13 performs foregoing step S207 to integrate the combination of feature point clusters (CG(1)) and (CG(2)) to which the time-series adjacent feature points C(1) and C(2) belong respectively, into one cluster.

Specifically, the area classification unit 13 first creates a new feature point cluster CG(1) having a minimum index ka (=1) as an index, from the feature point clusters (CG(1)) and (CG(2)). As illustrated in FIG. 5, the feature points C(1) and C(2) belong to the feature point cluster CG(1).

Then, the area classification unit 13 decrements the indexes of the feature point clusters (CG(3)) to (CG(6)) remaining after the foregoing integration process of feature point clusters, and performs a subtraction process on the total number Tk of feature point clusters. As a result, the original feature point clusters (CG(3)) to (CG(6)) are updated to feature point clusters (CG(2)) to (CG(5)), and the total number Tk=6 of feature point clusters is updated to the total number Tk=5.

After that, the area classification unit 13 repeatedly executes the foregoing process procedures at step S202 to S209 as appropriate to classify the original six feature points into three feature point clusters CG(1) to CG(3), as illustrated in FIG. 5. Specifically, as illustrated in FIG. 5, the original feature point clusters (C(1)) and (C(2)) belong to the feature point cluster CG(1); the original feature point clusters (C(3)) and (C(4)) belong to the feature point cluster CG(2); and the original feature point clusters (C(5)) and (C(6)) belong to the feature point cluster CG(3).

Further, the area classification unit 13 repeatedly performs foregoing steps S202 to S209 as appropriate to select the combination of feature point clusters CG(1) and CG(2) having a color difference equal to or less than the threshold value, as illustrated in FIG. 5. Then, from the selected combination of feature point clusters CG(1) and CG(2), the area classification unit 13 selects the combination of feature points C(2) and C(3) which belong to different feature point clusters and are closest to each other in time series.

In this arrangement, since the feature points C(2) and C(3) in combination are adjacent to each other as illustrated in FIG. 5, the area classification unit 13 performs the foregoing procedure at step S207 to integrate the feature point cluster CG(1) and feature point cluster CG(2) into one and the same cluster. Meanwhile, if selecting the combination of feature points C(4) and C(5) which belong to different feature point clusters and are closest to each other in time series from the combinations of feature point clusters CG(2) and CG(3), the area classification unit 13 does not integrate the feature point cluster CG(2) and the feature point cluster CG(3) because the feature points C(4) and C(5) in combination are not adjacent or identical to each other in time series.

After that, if the process of determining is completely performed on all the feature point clusters in the Lab-time series feature space, the area classification unit 13 terminates the process of classifying the interest areas in accordance with the foregoing process procedure at steps S201 to S209. As a result, the area classification unit 13 integrates the original feature point clusters (CG(1)) to (CG(4)) into one and the same feature point cluster CG(1) as illustrated in FIG. 6, and integrates the original feature point clusters (CG(5)) and (CG(6)) into one and the same feature point cluster CG(2).

In this arrangement, out of all the interest areas A(1, 1), A(2, 1), A(3, 1), A(4, 1), A(6, 1), and A(7, 1) in the in-vivo image group PG, the area classification unit 13 classifies the interest areas A(1, 1), A(2, 1), A(3, 1), and A(4, 1) into an area group corresponding to the feature point cluster CG(1), and classifies the interest areas A(6, 1) and A(7, 1) into an area group corresponding to the feature point cluster CG(2).

In addition, a plurality of interest areas belonging to one and the same feature point cluster, that is, a plurality of interest areas classified into one and the same area group, are similar in features such as color feature amounts and close to each other in time series. Meanwhile, a feature point cluster may be constituted by a single interest area. Interest areas corresponding to the single feature point belonging to the feature point cluster, are not similar in features such as color feature amounts and are distant from each other in time series, as compared with other interest areas included in the in-vivo image group PG.

Figure 7:
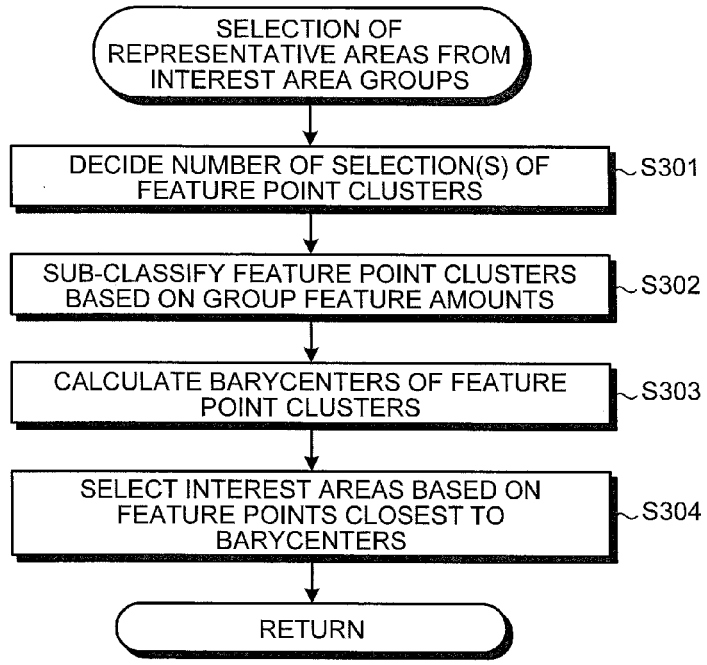
FIG. 7 is a flowchart illustrating an example of a processing procedure of selecting a representative area from the interest area group.
Figure 8:
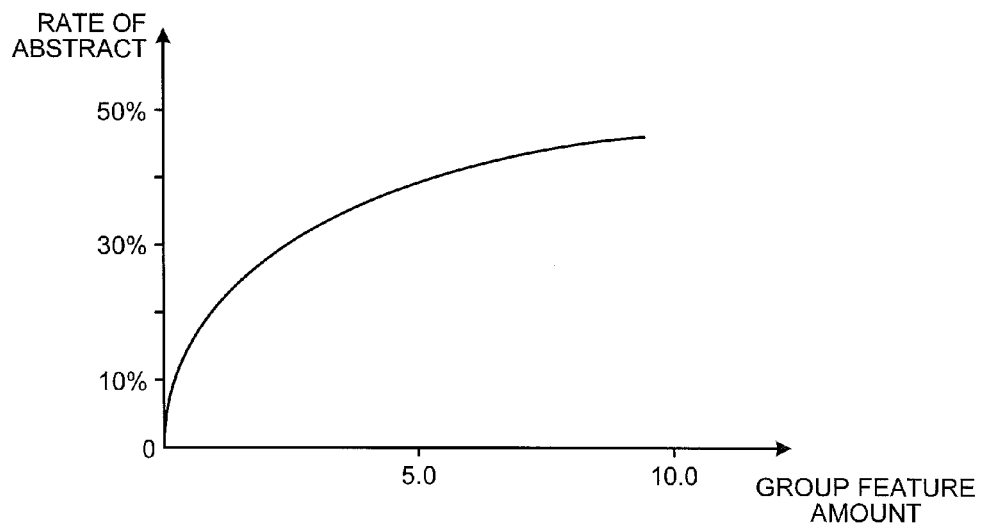
FIG. 8 is a schematic diagram illustrating a specific example of a function indicative of a relationship between the number of representative areas selected from the interest area groups and group feature amounts of the interest area groups.
Figure 9:
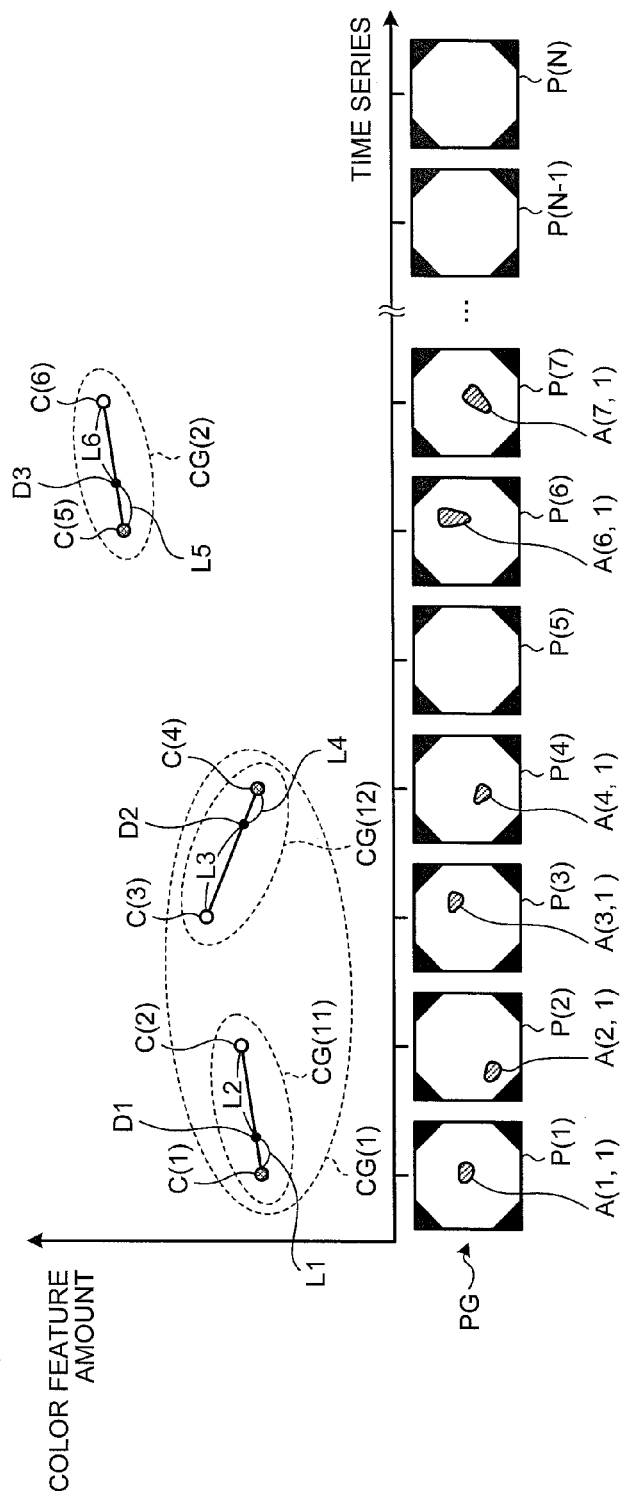
FIG. 9 is a schematic diagram describing that number of selection(s) of representative areas according to the group feature amounts are selected from the interest area groups.

Next, the foregoing process of selecting representative areas from the interest area groups at step S106 will be described in detail. FIG. 7 is a flowchart exemplifying the process procedure of selecting representative areas from the interest area groups. FIG. 8 is a schematic diagram illustrating one example of a function indicative of a relationship between the number of representative areas selected from the interest area groups and the group feature amounts of the interest feature amounts. FIG. 9 is a schematic diagram describing selection of a number of representative areas in accordance with the group feature amounts from the interest area groups. The area selection unit 15 of the image processing device 2 executes the process of selecting representative areas from the interest area groups at step S106 under control of the control unit 40, as described above.

Specifically, as illustrated in FIG. 7, the area selection unit 15 first executes a process of deciding the number of selection (s) of feature point clusters existing in the Lab-time series feature space (step S301). At step S301, the number-of-selection decision unit 15a decides the number of selection(s) of representative areas according to the group feature amounts calculated by the group feature amount calculation unit 14, for each of the area groups of the interest areas A(j, t) in the in-vivo image group PG.

Specifically, the function unit 15e holds in advance a function indicative of a relationship between the group feature amounts and the rate of abstract as illustrated in FIG. 8, for example. In this arrangement, the rate of abstract (vertical axis illustrated in FIG. 8) in this function refers to a value for deciding what % of the interest areas A(j, t) belonging to one area group as described above, which corresponds to the number of selection(s) of feature points from one and the same feature point cluster, that is, the number of selection(s) of representative areas from one and the same area group. The function unit 15e calculates the rate of abstract in accordance with the group feature amounts, for each of the area groups of the interest areas A(j, t).

Next, the number-of-selection decision unit 15a decides the number of selection(s) of representative areas of the interest areas A(j, t) in each of the area groups, based on the rate of abstract calculated for each of the area groups by the function unit 15e. Specifically, the number-of-selection decision unit 15a decides the number of selection(s) of representative feature points for each of the feature point clusters, based on the rate of abstract calculated for each of the feature point clusters.

After executing step S301, the area selection unit 15 executes the process of sub-classifying the feature point clusters based on the group feature amounts (step S302). At step S302, the sub-classification processing unit 15b sub-classifies the interest areas for each of the area groups into the same number of similarity groups as the number of selection(s) decided by the number-of-selection decision unit 15a, based on the average lightness index L(j, t) and average perception chromaticities a(j, t) and b(j, t) classified into each of the area groups by the area classification unit 13.

Specifically, the sub-classification processing unit 15b subjects the feature point clusters existing in the Lab-time series feature space to publicly known clustering such as k-means method, using the average lightness index L(j, t) and the average perception chromaticities a(j, t) and b(j, t) of the interest areas A(j, t) of feature points C(m) belonging to the feature point clusters, to sub-classify the feature points C(m) into the same number of feature point clusters as the foregoing number of selection(s).

In this arrangement, the feature point clusters sub-classified by the sub-classification processing unit 15b are groups corresponding to the foregoing similarity groups. Specifically, the feature points of the interest areas A(j, t) further similar to each other in color feature amount (for example, the feature points of identical interest areas) belong to the feature point clusters after the sub-classification process. The feature points in the feature point clusters corresponding to the similarity groups are similar to each other in the average lightness index L(k) and average perception chromaticities a(k) and b(k), as compared with the feature points in the other feature point clusters.

Meanwhile, after the execution of step S302, the area selection unit 15 executes the process of calculating barycenters of the feature point clusters in the Lab-time series feature space (step S303). At step S303, the barycenter calculation unit 15c calculates barycenters of feature amounts of a plurality of interest areas A(j, t) belonging to the similarity groups, for each of the similarity groups sub-classified by the sub-classification processing unit 15b.

Specifically, for each of the feature point clusters sub-classified by the sub-classification processing unit 15b, the barycenter calculation unit 15c calculates averages of color feature amount axis coordinate elements and an average of time-series axis coordinate elements for all the feature points belonging to the same feature point cluster after the sub-classification. The averages of color feature amount axis coordinate elements of feature points in the Lab-time series feature space refer to averages of the average lightness indexes L(j, t) and average perception chromaticities a(j, t) and b(j, t) of the interest areas A(j, t).

Then, for each of the feature point clusters after the sub-classification process, the barycenter calculation unit 15c calculates a barycenter having the calculated average of time-series axis coordinate elements as an axis element in a time-series axial direction and having the calculated average of color feature amount coordinate axis elements as an axis element in a color feature amount axial direction. In this arrangement, the barycenter of each of the feature point clusters after the sub-classification process has an average lightness index and average perception chromaticities of the same feature point cluster after the sub-classification, as coordinate elements in the color feature amount axial direction.

At step S303, out of all the feature point clusters in the Lab-time series feature space, the barycenter calculation unit 15c calculates the barycenters of the remaining feature clusters not sub-classified by the sub-classification processing unit 15b as in the case of the feature point clusters after the sub-classification process. The remaining not-classified feature point clusters may be feature point clusters to which only two feature points with high similarity belong, or the like, for example.

After the execution of step S303, the area selection unit 15 executes the process of selecting interest areas based on the feature points closest to the barycenters of the feature point clusters (step S304). After that, the area selection unit 15 terminates this process and returns to the process procedure at step S106 illustrated in FIG. 2.

At step S304, for each of the foregoing similarity groups, from a plurality of interest areas A(j, t) included in the same similarity group, the closest area selection unit 15d selects an interest area closest to the barycenter of feature amounts calculated by the barycenter calculation unit 15c, as compared with the other interest areas.

Specifically, for each of the feature point clusters sub-classified by the sub-classification processing unit 15b, the closest area selection unit 15d first calculates separation distances between a plurality of feature points belonging to the same feature point cluster after the sub-classification and the barycenter. In this arrangement, the separation distances calculated by the closest area selection unit 15d refers to Euclidean distances between the feature points in the same feature point cluster and the barycenters calculated by the barycenter calculation unit 15c in the Lab-time series feature space.

Then, for each of the sub-classified feature point clusters, the closest area selection unit 15d compares the separation distances between the feature points and the barycenter and selects a feature point closest to the barycenter. As a result, for each of the feature point clusters in the Lab-time series feature space, the closest area selection unit 15d selects the same number of feature points as the number of selection(s) decided by the number-of-selection decision unit 15a.

After that, the closest area selection unit 15d selects the interest area A(j, t) corresponding to the selected feature point from each of the similarity groups as described above. Consequently, from each of the similarity groups in the in-vivo image group PG, the closest area selection unit 15d selects the same number of the interest areas A(j, t) as the number of selection(s) for the similarity group.

At step S304, for each of the remaining area groups not classified into the similarity groups, the closest area selection unit 15d also selects interest areas closest to the barycenters of the feature amounts calculated by the barycenter calculation unit 15c as compared with the other interest areas, from a plurality of interest areas A(j, t) included in the same area group, as in the case of the foregoing similarity groups.

Specifically, for each of the remaining feature point clusters not sub-classified by the sub-classification processing unit 15b, the closest area selection unit 15d first calculates separation distances between a plurality of feature points belonging to the same feature point cluster and the barycenter. Next, the closest area selection unit 15d compares the separation distances between the feature points and the barycenter for each of the remaining feature point clusters, and selects a feature point closest to the barycenter. As a result, the closest area selection unit 15d selects the same number of feature points as the foregoing number of selection(s), for each of the remaining feature point clusters.

After that, the closest area selection unit 15d selects the interest area A(j, t) corresponding to the selected feature point in each of the area groups as described above. As a result, the closest area selection unit 15d selects the same number of interest areas A(j, t) as the number of selection(s) from each of the area groups in the in-vivo image group PG.

As in the foregoing, the area selection unit 15 sets the interest areas A(j, t) selected by the closest area selection unit 15d as representative areas of the area groups or the similarity groups, and transmits results of the process of selecting the representative areas to the representative image output unit 16.

Referring to FIG. 9, the process procedures at steps S301 to S304 executed by the area selection unit 15 will be described in detail. As illustrated in FIG. 9, if there exist the feature point cluster CG(1) including the feature points C(1) to C(4) and the feature point cluster CG(2) including the feature points C(5) and C(6) in the Lab-time series feature space, the area selection unit 15 performs the process procedure at step S301 to decide the number of selection(s) V for both the two feature point clusters CG(1) and CG(2).

Specifically, the number-of-selection decision unit 15a decides the number of selection(s) V (=2) for the feature point cluster CG(1) in accordance with the group feature amounts of the feature point cluster CG(1) and the number of selection(s) V (=1) for the feature pint cluster CG(2) in accordance with the group feature amounts of the feature point cluster CG(2), based on the rate of abstract calculated by the function unit 15e(see FIG. 8).

Next, the area selection unit 15 performs the process procedure at step S302 to sub-classify the feature point clusters CG(1) and CG(2). Specifically, since the number of selection(s) V for the feature point cluster CG(1) decided by the number-of-selection decision unit 15a at step S301 is "2," the sub-classification processing unit 15b sub-classifies the feature points C(1) to C(4) into two feature point clusters CG(11) and CG(12) which are the same number as the number of selection(s) V (=2), as illustrated in FIG. 9, based on the color feature amounts of the feature points C(1) to C(4) belonging to the feature point cluster CG(1). As a result, out of all the feature points C(1) to C(4) in the feature point clusters CG(1), the two feature points C(1) and C(2) with higher similarity in color feature amounts than the other feature points C(3) and C(4), are sub-classified into one and the same feature point cluster CG(11), and the two feature points C(3) and C(4) with higher similarity in color feature amounts than the other feature points C(1) and C(2), are sub-classified into one and the same feature point cluster CG(12).

Meanwhile, since the number of selection(s) V for the feature point cluster CG(2) decided by the number-of-selection decision unit 15a at step S301 is "1", the feature point cluster CG(2) is sub-classified into one feature point cluster. Specifically, the sub-classification processing unit 15b does not further sub-classify the feature points C(5) and C(6) belonging to the feature point cluster CG(2) but maintains this group state, as illustrated in FIG. 9.

Subsequently, the area selection unit 15 performs the process procedure at step S303 to calculate barycenters of the feature point clusters in the Lab-time series feature space. Specifically, the barycenter calculation unit 15c calculates barycenters D1, D2, and D3 of the feature point clusters CG(11), CG(12), and CG(2) respectively, as illustrated in FIG. 9.

For more detail, the barycenter calculation unit 15c calculates averages of time-series axis coordinate elements and averages of color feature amount axis coordinate elements of the two feature points C(1) and C(2) belonging to the feature point cluster CG(11). Similarly, the barycenter calculation unit 15c calculates averages of time-series axis coordinate elements and averages of color feature amount axis coordinate elements of the two feature points C(3) and C(4) belonging to the feature point cluster CG(12). In addition, the barycenter calculation unit 15c calculates averages of time-series axis coordinate elements and averages of color feature amount axis coordinate elements of the two feature points C(5) and C(6) belonging to the feature point cluster CG(2). The averages of time-series axis coordinate elements calculated by the barycenter calculation unit 15c refer to coordinate elements in a time-series axial direction of the barycenters D1 to D3, and the averages of color feature amount axis coordinate elements refer to coordinate elements in a color feature amount axial direction of the barycenters D1 to D3.

After that, the area selection unit 15 performs the process procedure at step S304 to select representative interest areas based on the feature point closest to the barycenter of each of the feature point clusters in the Lab-time series feature space. Specifically, for each of the similarity groups or the area groups of the interest areas corresponding to the feature points clusters CG(11), CG(12), and CG(2) illustrated in FIG. 9, the closest area selection unit 15d selects an interest area closest to the barycenter of feature amounts calculated by the barycenter calculation unit 15c as compared with other interest areas.

Specifically, the closest area selection unit 15d first calculates a separation distance L1 between the feature point C(1) and the barycenter D1 and a separation distance L2 between the feature point C(2) and the barycenter D1 in one feature point cluster CG(11) belonging to the feature point cluster CG(1). Then, the closest area selection unit 15d compares the calculated separation distances L1 and L2 (L1<L2) and selects the feature point closest to the barycenter D1, that is, the feature point C(1) at the smaller separation distance. Next, the closest area selection unit 15d calculates a separation distance L3 between the feature point C(3) and the barycenter D2 and a separation distance L4 between the feature point C(4) and the barycenter D2 in the other feature point cluster CG(12) belonging to the feature point cluster CG(1). Then, the closest area selection unit 15d compares the calculated separation distances L3 and L4 (L3>L4), and selects the feature point closest to the barycenter D2, that is, the feature point C(4) at the smaller separation distance. As a result, the closest area selection unit 15d selects the two feature points C(1) and C(4) which are the same number as the number of selections V (=2) in the feature point cluster CG(1) from the feature point cluster CG(1).

Next, the closest area selection unit 15d selects the interest area A(1, 1) corresponding to the feature point C(1) from the similarity group of the interest areas corresponding to the feature point cluster CG(11), and selects the interest area A(4, 1) corresponding to the feature point C(4) from the similarity group of the interest areas corresponding to the feature point cluster CG(12). Specifically, the closest area selection unit 15d selects two interest areas A(1, 1) and A(4, 1) which are the same number as the number of selections V (=2) in the feature point cluster CG(1) from the in-vivo image group PG.

Subsequently, the closest area selection unit 15d calculates a separation distance L5 between the feature point C(5) and the barycenter D3 and a separation distance L6 between the feature points C(6) and the barycenter D3 in the remaining feature point cluster CG(2). Then, the closest area selection unit 15d compares the calculated separation distances L5 and L6 (L5<L6), and selects the feature point closest to the barycenter D3, that is, the feature point C(5) at the smaller separation distance. As a result, the closest area selection unit 15d selects the one feature point C(5) which is the same number as the number of selection V (=1) in the feature point cluster CG(2) from the feature point cluster CG(2). Next, the closest area selection unit 15d selects an interest area A(6, 1) corresponding to the feature point C(5) from the area group of the interest areas corresponding to the feature point cluster CG(2). Specifically, the closest area selection unit 15d selects the one interest area A(6, 1) which is the same number as the number of selection V (=1) in the feature point cluster CG(1) from the in-vivo image group PG.

As illustrated in FIG. 9, the interest areas A(1, 1) and A(2, 1) in the in-vivo image group PG belong to the similarity group of the interest areas corresponding to feature point cluster CG(11), and the interest areas A(3, 1) and A(4, 1) in the in-vivo image group PG belong to the similarity group of the interest areas corresponding to the feature point cluster CG(12). In addition, the interest areas A(6, 1) and A(7, 1) in the in-vivo image group PG belong to the area group of the interest areas corresponding to the feature point cluster CG(2).

After that, the area selection unit 15 selects the interest areas A(1, 1), A(4, 1), and A(6, 1) selected by the closest area selection unit 15d as representative areas of the area group or the similarity groups in the in-vivo image group PG, and transmits results of the process of selecting the representative areas to the representative image output unit 16.

In addition, from the in-vivo image group PG, the representative image output unit 16 outputs to the display device 3 an in-vivo image P(1) including the interest area A(1, 1) as a representative area, an in-vivo image P(4) including the interest area A(4, 1), and an in-vivo image P(6) including the interest area A(6, 1), as an representative in-vivo image group to be displayed, based on results of the process of selecting the representative areas acquired from the area selection unit 15.

As described above, the first embodiment of the present invention is configured to classify interest areas into area groups, based on feature amounts of the interest areas and time-series positions of in-vivo images including the interest areas, select representative areas from the classified interest areas belonging to the area groups, and output representative images including the representative areas.

Accordingly, by classifying the interest areas in consideration of the feature amounts of the interest areas and time-series positions of in-vivo images including the interest areas, it is possible to bring together interest areas similar in feature amount and close to each other in time series (e.g. identical lesion areas detected within a predetermined period of time), into one area group, for example. In addition, by outputting the representative images including the representative areas selected from the similar interest areas in the area group, for example, it is possible to eliminate a wasteful operation of outputting the in-vivo images including the similar interest images many times. This reduces an observer's burden of observing the images.

Further, in the first embodiment of the present invention, since representative areas of representative images to be output are selected from at least interest areas with a high degree of necessity for observation, it is possible to eliminate the possibility that images including non-interest areas with a low degree of necessity for observation, thereby eliminating a wasteful operation of observing images including non-interest areas with a low degree of necessity for observation. This reduces an observer's burden of observing the images.

Second Embodiment

Next, a second embodiment of the present invention will be described. In the foregoing first embodiment, the number of selection(s) is decided in accordance with group feature amounts of area groups of interest areas; the area groups of interest areas are sub-classified into the same number of group(s) as the decided number of selection(s); representative areas are selected from the sub-classified groups of interest areas; and the same number of representative area(s) as the number of selection(s) are selected. Meanwhile, in the second embodiment, time-series coordinates are calculated for dividing the feature point clusters at equal distances in a time-series direction in accordance with the foregoing number of selection(s), and interest areas corresponding to feature points closest to the obtained time-series coordinates are selected, thereby selecting the same number of representative area(s) as the number of selection(s).

Figure 10:
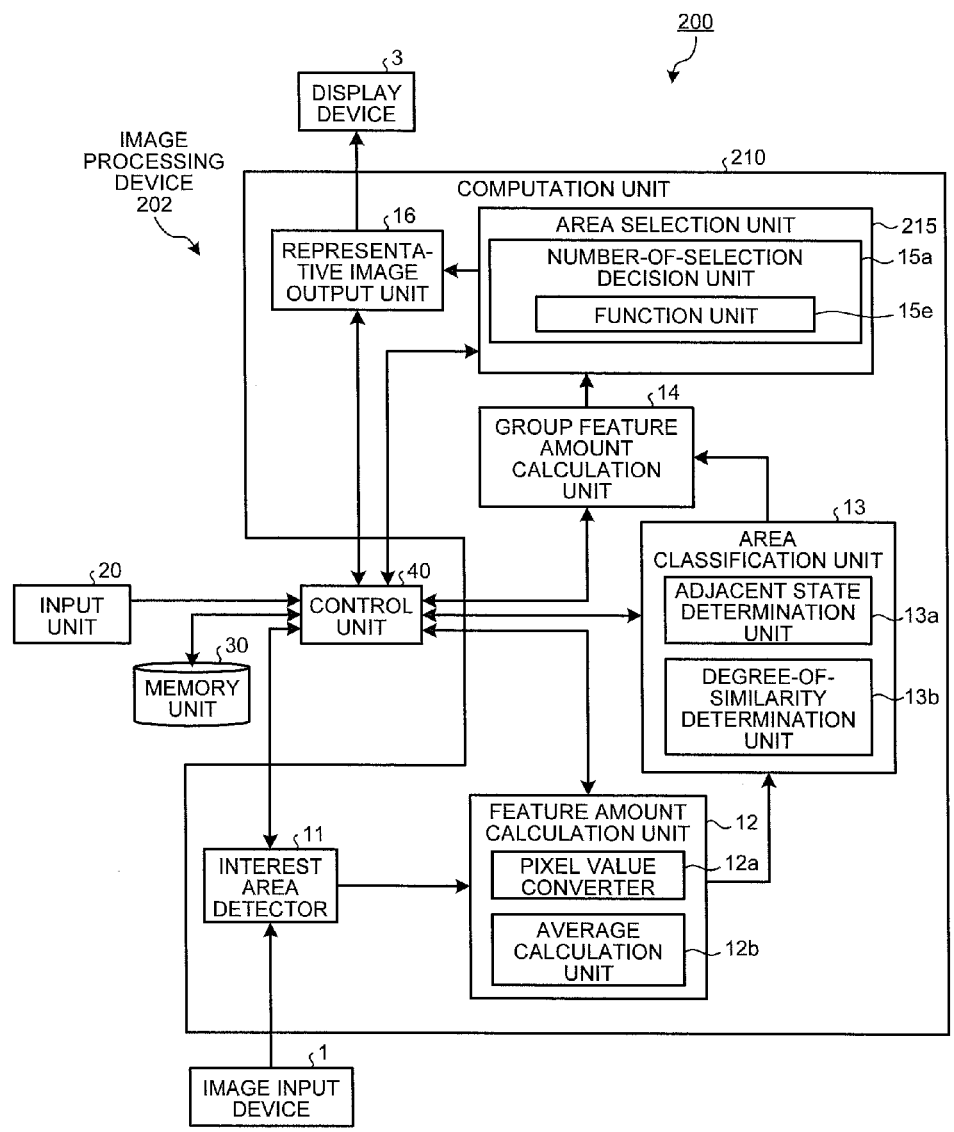
FIG. 10 is a block diagram schematically illustrating a configuration example of an image display system including an image processing device according to a second embodiment of the present invention.

FIG. 10 is a block diagram illustrating schematically one configuration example of an image display system, including an image processing device in the second embodiment of the present invention. As illustrated in FIG. 10, an image display system 200 in the second embodiment includes an image processing device 202 instead of the image processing device 2 of the image display system 100 in the foregoing first embodiment. The image processing device 202 includes a computation unit 210 instead of the computation unit 10 of the image processing device 2 in the first embodiment. The computation unit 210 includes an area selection unit 215 instead of the area selection unit 15 of the computation unit 10 in the first embodiment. Other components in the second embodiment are identical to those in the first embodiment and are given the same reference numerals as those in the first embodiment.

The image processing device 202 includes the computation unit 210 instead of the computation unit 10 of the image processing device 2 in the first embodiment, as described above. In addition, the computation unit 210 includes the area selection unit 215 instead of the area selection unit 15 of the computation unit 10 in the first embodiment. The image processing device 202 has the functions of the computation unit 210 and the same functions as those of the image processing device 2 in the foregoing first embodiment. In addition, the computation unit 210 has the functions of the area selection unit 215 and the same functions as those of the computation unit 10 in the foregoing first embodiment.

The area selection unit 215 includes the number-of-selection decision unit 15a similar to the area selection unit 15 in the foregoing first embodiment, as illustrated in FIG. 10. Meanwhile, the area selection unit 215 does not include the sub-classification processing unit 15b, the barycenter calculation unit 15c, or the closest area selection unit 15d in the foregoing first embodiment. That is, the number-of-selection decision unit 15a has the same function of deciding the number of selection(s) as that of the area selection unit 15 in the first embodiment, and is different from the area selection unit 15 in the first embodiment only in that the number-of-selection decision unit 15a does not have the function of selecting representative areas from interest area groups in accordance with the decided number of selection(s) for area groups of interest areas. The thus configured area selection unit 215 selects the same number of representative area(s) as the number of selection(s) decided by the number-of-selection decision unit 15a from area groups, by performing a process procedure different from that of the area selection unit 15 in the first embodiment.

Specifically, the area selection unit 215 calculates time-series coordinates for dividing distribution of feature amounts of a plurality of interest areas A(j, t) in the in-vivo image group PG at equal distance in a time-series direction, in correspondence with the number of selection(s) decided by the number-of-selection decision unit 15a, and selects the same number of interest area(s) closest to the time-series coordinates as the number of selection(s), as representative areas of the plurality of interest areas A(j, t).

Next, an operation of the image processing device 202 in the second embodiment of the present invention will be described. The image processing device 202 operates in the same manner as the image processing device 2 in the first embodiment, except for an operation of the area selection unit 215 in the computation unit 210 as described above. That is, the image processing device 202 performs the approximately same process procedures as step S101 to S107 illustrated in FIG. 2, thereby to output one or more representative in-vivo images to the display device 3. Specifically, the image processing device 202 is different from the image processing device 2 in the first embodiment, only in the process procedure at step S106. The process procedure at step S106 executed by the image processing device 202 in the second embodiment will be described below in detail.

FIG. 11 is a flowchart exemplifying a procedure of process of selecting representative areas in interest area groups in the second embodiment. FIG. 12 is a schematic diagram describing specifically the process of selecting representative areas in the second embodiment.

A feature space illustrated in FIG. 12 is a Lab-time series feature space. In FIG. 12, for sake of simplicity in description of the present invention, an average lightness index L(j, t) and average perception chromaticities a(j, t) and b(j, t) of the interest areas A(j, t) are collectively represented in one axis as color feature amounts.

The area selection unit 215 of the image processing device 202 executes sequentially the process procedures at step S401 to S403 illustrated in FIG. 11 under control of the control unit 40, thereby to achieve the process of selecting representative areas in the interest area groups at step S106 illustrated in FIG. 2.

Specifically, as illustrated in FIG. 11, the area selection unit 215 first executes the process of deciding the number of selection(s) of feature point clusters existing in the Lab-time series feature space, as in the case of the first embodiment (step S401). At step S401, the number-of-selection decision unit 15a decides the number of selection(s) V of representative areas in accordance with the group feature amounts calculated by the group feature amount calculation unit 14 for the area groups of the interest areas A(j, t) in the in-vivo image group PG, as at step S301 illustrated in FIG. 7.

After executing step S401, the area selection unit 215 executes the process of calculating time-series coordinates dividing feature point clusters at equal distances in a time-series direction, in accordance with the number of selection(s) V decided by the number-of-selection decision unit 15a (step S402).

At step S402, the area selection unit 215 first sets the index k of feature point cluster CG(k) in the Lab-time series feature space at an initial value (=1), and determines a minimum value Tmin and a maximum value Tmax of coordinate elements in a time-series direction (that is, time-series coordinates) of all feature points belonging to the feature point cluster CG(1).

Then, the area selection unit 215 divides a difference between the maximum value Tmax and the minimum value Tmin of the time-series coordinates (Tmax−Tmin) by a value in which "1" is added to the number of selection(s) V of the feature point cluster CG(1) decided by the number-of-selection decision unit 15a (V+1). In this arrangement, the area selection unit 215 sets the value obtained by the division process as a step width W in a time-series direction.

After that, the area selection unit 215 sets an index of time-series coordinates T(1, i) dividing the feature point cluster CG(1) at an initial value (=1), and calculates sequentially the time-series coordinates T(1, i) in the feature point cluster CG(1) (k=1, 1≤i≤V) in accordance with Equation (3) shown below, while incrementing the index i sequentially until the index i becomes equal to the number of selection(s) V of the feature point cluster CG(1).

$$T(k,i) = T\min + W \times i \, (1 \leq k \leq Tk, 1 \leq i \leq V) \quad (3)$$

After calculating the time-series coordinates T(1, i) in the feature point cluster CG(1), the area selection unit 215 executes repeatedly the foregoing computation process in accordance with Equation (3), while incrementing sequentially the index k of the feature point cluster CG(k) up to the total number Tk of the feature point clusters. As a result, the area selection unit 215 calculates the same number of time-series coordinates T(k, i) as the number of selection(s) V decided by the number-of-selection decision unit 15a, for each of the feature point clusters CG(k) existing in the Lab-time series feature space.

In this arrangement, the time-series coordinates T(k, i) for the feature point clusters CG(k) divide distribution of feature points belonging to the feature point cluster CG(k) at equal distances in a time-series direction. Specifically, the time-series coordinates T(k, i) for the feature point cluster CG(k) divide distribution of feature amounts of a plurality of interest areas corresponding to the feature point cluster CG(k) at equal distances in a time-series direction.

After executing step S402, the area selection unit 215 executes the process of selecting interest areas based on feature points closest to the time-series coordinates T(k, i), for each of the feature point clusters CG(k) in the Lab-time series feature space (step S403). After that, the area selection unit 215 terminates the process and returns to step S106 illustrated in FIG. 2.

At step S403, the area selection unit 215 first calculates separation distances between feature points belonging to the feature point clusters CG(k) and the time-series coordinates T(k, i), for each of the feature point clusters CG(k) in the Lab-time series feature space. Next, for each of the feature point clusters CG(k), the area selection unit 215 compares the calculated separation distances sequentially in prescribed order (for example, in time series) and selects feature points at a minimum separation distance, that is, the same number of feature points closest to the time-series coordinates T(k, i) as the number of selection(s) V for the feature point cluster CG(k). Then, the area selection unit 215 selects interest areas corresponding to the selected feature points from the in-vivo image group PG. As a result, the area selection unit 215 selects the same number of interest areas A(j, t) as the number of selection(s) V as representative areas of the area groups, for each of the area groups of interest areas in the in-vivo image group PG. The area selection unit 215 transmits results of the process of selecting the representative areas, to the representative image output unit 16.

Referring to FIG. 12, the process procedures at step S401 to S403 executed by the area selection unit 215 will be specifically described. As illustrated in FIG. 12, if there exist the feature point cluster CG(1) including feature points C(1) to C(4) and the feature point cluster CG(2) including feature points C(5) and C(6) in the Lab-time series feature space as illustrated in FIG. 12, the area selection unit 215 performs the process procedure at step S401 to thereby decide the number of selection(s) V for the two feature point clusters CG(1) and CG(2).

Specifically, the number-of-selection decision unit 15a first decides the number of selections V (=2) for the feature point clusters CG(1) according to group feature amounts of the feature cluster CG(1) and the number of selection V (=1) for the feature point cluster CG(2) according to the group feature amounts of the feature point cluster CG(2).

Next, the area selection unit 215 performs the process procedure at step S402 to thereby calculate time-series coordinates of the feature point cluster CG(1) and the feature point cluster CG(2) in the Lab-time series feature space. Specifically, the area selection unit 215 first determines a minimum value Tmin and a maximum value Tmax of the time-series coordinates of the feature points C(1) to C(4) belonging to the feature point cluster CG(1). In this arrangement, the minimum value Tmin resides in a coordinate element of a time-series axis of the feature point C(1) with a smallest index in the feature point cluster CG(1), and the maximum value Tmax resides in a coordinate element of a time-series axis of the feature point C(4) with a largest index in the feature point cluster CG(1).

Then, the area selection unit 215 divides a difference between the maximum Tmax and the minimum Tmin (Tmax−Tmin) of the time-series coordinates by a value (=3) in which "1" is added to the number of selections V (=2) in the feature point cluster CG(1), thereby to calculate a step width W in a time-series direction in the feature point cluster CG(1). The area selection unit 215 uses the number of selections V (=2) for the feature point cluster CG(1) and the parameters such as the minimum value Tmin and the step width W of the time-series coordinates, thereby to calculate two time-series coordinates T(1, 1) and T(1, 2) which are the same number as the number of selections V (=2) for the feature point cluster CG(1), in accordance with following Equation (3).

In this arrangement, as shown in FIG. 12, the time-series coordinates T(1, 1) and T(1, 2) divide distribution of the feature points C(1) to C(4) in the feature point cluster CG(1) at equal distances in a time-series axial direction. That is, the time-series coordinates T(1, 1) and T(1, 2) divide distribution of feature amounts of the four interest areas A(1, 1) to A(4, 1) in the in-vivo image group PG corresponding to the four feature points C(1) to C(4) at equal distances in a time-series axial direction.

Subsequently, the area selection unit 215 determines a minimum value Tmin and a maximum value Tmax of the time-series coordinates of the two feature points C(5) and C(6) belonging to the remaining feature point cluster CG(2). In this arrangement, the minimum value Tmin resides in a coordinate element of a time-series axis of the feature point C(5) with the minimum index in the feature point cluster CG(2), and the maximum value Tmax resides in a coordinate element of a time-series axis of the feature point C(6) with the maximum index in the feature point cluster CG(2).

Next, the area selection unit 215 divides a difference between the maximum Tmax and the minimum Tmin (Tmax−Tmin) of the time-series coordinates by a value (=2) in which "1" is added to the number of selection V (=1) for the feature point cluster CG(2), thereby calculating a step width W in a time-series direction in the feature point cluster CG(2). The area selection unit 215 uses parameters such as the number of selection V (=1), the minimum value Tmin and the step width W of the time-series coordinates, to calculate one time-series coordinate (2, 1) which is the same number of the number of selection V (=1) for the feature point cluster CG(2), in accordance with Equation (3).

In this arrangement, the time-series coordinate T(2, 1) divides distribution of the two feature points C(5) and C(6) in the feature point cluster CG(2) at equal distances in a time-series axial direction, as illustrated in FIG. 12. That is, the time-series coordinate T(2, 1) divides distribution of the feature amounts of the two interest areas A(6, 1) and A(7, 1) in the in-vivo image group PG corresponding to the two feature points C(5) and C(6).

After that, the area selection unit 215 performs the process procedure at step S403 to select interest areas based on feature points closest to the two time-series coordinates T(1, 1) and T(1, 2) in the feature point cluster CG(1), and selects an interest area based on a feature point closest to the one time-series coordinate T(2, 1) in the feature point cluster CG(2).

Specifically, the area selection unit 215 first separation distances between four feature points C(1) to C(4) belonging to the feature point cluster CG(1) with a smaller index and one time-series coordinate T(1, 1) out of the two time-series coordinates T(1, 1) and T(1, 2). Next, the area selection unit 215 compares sequentially the calculated separation distances in prescribed order (for example, in time series), and selects a feature point at a minimum separation distance from the time-series coordinate T(1, 1), that is, the feature point C(2) closest to the time-series coordinate (1, 1), from the feature point cluster CG(1).

Next, the area selection unit 215 calculates separation distances between the four feature points C(1) to C(4) belonging to the feature point cluster CG(1) and the other time-series coordinate T(1, 2) out of the two time-series coordinates T(1, 1) and T(1, 2). Then, the area selection unit 215 compares sequentially the calculated separation distances in prescribed order (for example, in time series), and selects a feature point at a minimum separation distance from the time-series coordinate T(1, 2), that is, the feature point C(3) closest to the time-series coordinate T(1, 2), from the feature point cluster CG(1).

As in the foregoing, the area selection unit 215 selects the two feature points C(2) and C(3) which are the same number as the number of selections V (=2) in the feature point cluster CG(1), from the feature point cluster CG(1). Subsequently, the area selection unit 215 selects the two interest areas A(2, 1) and A(3, 1) which correspond to the two selected feature points C(2) and C(3), respectively, from the in-vivo image group PG.

Next, the area selection unit 215 calculates separation distances between the two feature points C(5) and C(6) belonging to the feature point cluster CG(2) with a smallest index following that of the already processed feature point cluster CG(1) and one time-series coordinate T(2, 1). Subsequently, the area selection unit 215 compares the calculate separation distances sequentially in prescribed order (for example, in time series), and selects a feature point at a minimum separation distance from the time-series coordinate T(2, 1), that is, the feature point C(5) closest to the time-series coordinate (2, 1), from the feature point cluster CG(2).

As in the foregoing, the area selection unit 215 selects the one feature point C(5) which is the same number as the number of selection V (=1) of the feature point cluster CG(2), from the feature point cluster CG(2). Subsequently, the area selection unit 215 selects the one interest area A(6, 1) corresponding to the selected one feature point C(5), from the in-vivo image group PG.

In this arrangement, as described above, the area selection unit 215 executes the process of selecting representative areas on all the feature point clusters CG(1) and CG(2) in the Lab-time series feature space, thereby to select the same number of interest areas A(j, t) as the number of selection(s) V for each of the area groups in the in-vivo image group PG.

Specifically, the area selection unit 215 selects total three interest areas as representative areas in the area groups of the interest areas: the interest areas A(2, 1) and A(3, 1) which are the same number as the number of selections V=2 and the interest area A(6, 1) which is the same number as the number of selection V=1. The area selection unit 215 transmits results of the process of selecting the representative areas to the representative image output unit 16.

Meanwhile, the representative image output unit 16 outputs an in-vivo image P(2) including the interest area A(2, 1) as a representative area, an in-vivo image P(3) including the interest area A(3, 1), and an in-vivo image P(6) including the interest area A(6, 1), as a representative in-vivo image group to be displayed, to the display device 3.

If there exists a plurality of feature points at a minimum separation distance from the time-series coordinate T(k, i) in the same feature point cluster CG(k), the area selection unit 215 can select either one of these plurality of feature points in accordance with a prescribed method. For example, out of the plurality of feature points at a minimum separation distance from the time-series coordinate T(k, i), the area selection unit 215 may select the oldest feature point (that is, having a smallest index) in time series, or may select a latest feature point (that is, having a largest index) in time series. In either case, the area selection unit 215 is only required to select one feature point for each of the time-series coordinates T(k, i).

As described above, the second embodiment of the present invention is configured to: calculate time-series coordinates which are the same number of the number of selections decided in accordance with group feature amounts of area groups of interest areas included in an in-vivo image group, and divide distribution of feature amounts of the interest areas in the area group corresponding to feature point clusters in the Lab-time series feature space; and select interest areas in the in-vivo image group for the time-series coordinates which are the same number as the number of selections, as representative areas of the interest areas in the in-vivo image group. In the other respects, the second embodiment is configured in the same manner as the first embodiment.

This produces the same effect and advantage as those of the foregoing first embodiment. In addition, since the same number of interest areas as the foregoing number of selections are selected as representative areas without sub-classifying again feature point clusters in the Lab-time series feature space, interest areas can be selected from the in-vivo image group in a shorter time as compared with the case of the first embodiment. As a result, it is possible to realize an image processing device, an image processing program, and an image processing method, which further facilitate shortening of a processing time required for outputting in-vivo images including interest areas to be observed.

In foregoing Embodiments 1 and 2, a single interest area is included as an object in a single in-vivo image. However, the present invention is not limited to this but may be configured such that a plurality of interest areas is included in a single in-vivo image. For example, if a plurality of interest areas A(j, t) (t≥2) is included as an object in an in-vivo image P(j) in the foregoing in-vivo image group PG, the plurality of interest areas A(j, t) is identified by two or more indexes. Specifically, if the number of interest areas included in the in-vivo image P(j) is two, these interest areas are identified by the same number of indexes t as the number of interest areas, such as the interest areas A(j, 1) and A(j, 2). The time-series coordinates of a plurality of interest areas included in one and the same in-vivo image have an identical value.

In addition, in foregoing Embodiments 1 and 2, the pixel value converter 12a converts the values of RGB color spaces in the in-vivo images to be processed, into the values of L*a*b* space. However, the present invention is not limited to this, and the pixel value converter 12a may convert the values of RGB color space in the in-vivo images to be processed, into the values of color space other than the L*a*b* space, for example, the values of Yuv color space or the values of HSI color space.

Further, in foregoing Embodiments 1 and 2, color feature amounts are exemplified as one example of feature amounts of interest areas such as lesion areas. However, the present invention is not limited to this, and the foregoing feature amounts of interest areas may be shape feature amounts such as the degree of circular form of interest areas, structure feature amounts such as boundary length, or position feature amounts such as position information of interest areas in in-vivo images, or a combination of at least two of the same.

In addition, in foregoing Embodiments 1 and 2, the sum total Sum(k) of dispersions of the average lightness index and average perception chromaticities as color feature amounts of interest areas (or feature points), are set as group feature amounts of the area groups of the interest areas. However, the present invention is not limited to this, and the foregoing group feature amount calculation unit 14 may calculate averages of dispersions of color feature amounts of interest areas as group feature amounts, or may calculate sum total or averages of standard deviations of color feature amounts of interest areas as group feature amounts. Alternatively, the group feature amount calculation unit 14 may calculate group feature amounts by factoring (for example, adding) dispersions of interest areas in a time-series direction, into the values of dispersions or standard deviations or the like based on the foregoing color feature amounts of interest areas.

Further, in foregoing Embodiments 1 and 2, the number of selection(s) of representative interest areas (that is, representative areas) is decided in accordance with group feature amounts of area groups to which interest areas such as lesion areas belong. However, the present invention is not limited to this, and the number of selection(s) of representative areas may be decided in accordance with variations in feature amounts (for example, color feature amounts) of feature points or interest areas belonging to feature point clusters. In addition, images in an in-vivo image group captured sequentially in time series without movement of a capsule endoscope in the inside of body of a subject, have few variations in feature amount such as color, shape, and the like of captured interest areas. Meanwhile, images in an in-vivo image group captured sequentially in time series with movements of a capsule endoscope in the inside of body of a subject, have some variations in feature amount such as color, shape, and the like of captured interest areas. That is, the in-vivo image group captured by a capsule endoscope with movements, produces more variations in vision of interest areas and have more interest information to be observed. Accordingly, if an in-vivo image group captured by a capsule endoscope with movements is to be processed, it is desired to change the number of selection(s) of representative areas in accordance with variations in feature amounts of feature points or interest areas belonging to feature point clusters in the Lab-time series feature space.

In addition, in the second embodiment, time-series coordinates are calculated in accordance with foregoing Equation (3). However, the present invention is not limited to this, and the foregoing time-series coordinates may be frame numbers (image numbers) of in-vivo images in an in-vivo image group captured in time series. If a plurality of interest areas with similar features is included as objects in in-vivo images with the same frame number, interest areas to be selected as representative areas may be any of the plurality of interest areas.

Further, in foregoing Embodiments 1 and 2, feature points of interest areas are distributed in a feature space formed by coordinate axes of color feature amounts (for example, average lightness index, average perception chromaticities, and the like, in the L*a*b* space) and time-series coordinate axes of interest areas. However, the present invention is not limited to this, and feature points of interest areas in the present invention may be distributed in a feature space by two of coordinate axes of color feature amounts of interest areas, shape feature amounts such as the degree of circularity of interest areas, structure feature amounts such as boundary length of interest areas, position feature amounts such as position information of interest areas, and time-series coordinate axes. For example, the feature points of interest areas may be distributed in a feature space formed by coordinate axes of color feature amounts and shape feature amounts, or may be distributed in a feature space formed by coordinate axes of shape feature amounts and time-series positions.

In addition, in relation to foregoing Embodiments 1 and 2, an in-vivo image group of a subject is described as one example of a time-series image group to be processed. However, the present invention is not limited to this, and a time-series image group to be processed in the present invention may not be an in-vivo image group in which the inside of body of a subject, such as the inside of a digestive tract, is captured in time series but the object to be imaged may be a desired one other than the inside of a subject such as the inside of the digestive tract. That is, interest areas included in the time-series image group may not be limited to areas of the inside of body of a subject but may be desired areas to be observed by an observer. In addition, the foregoing image input device 1 is not limited to an input device for inputting an in-vivo image group captured by a capsule endoscope into an image processing device, but may be a device for storing a time-series image group of a desired subject and inputting the time-series image group into an image processing device, or may be an electronic imaging device such as a digital camera for imaging a time-series image group and inputting the obtained time-series image group into an image display device.

Further, in foregoing Embodiments 1 and 2, representative images including interest areas out of a time-series image group are output as time-series images to be displayed to the display device 3. However, the present invention is not limited to this, and an image processing device, an image processing program, and an image processing method according to the present invention, may be intended to output representative images including interest areas out of a time-series image group as time-series images to be stored to a memory device or may be intended to output representative images including interest areas out of a time-series image group as time-series images to be printed to a printer. That is, a device receiving representative images including interest areas from an image processing device according to the present invention is not limited to the foregoing display device 3 but may be a memory device such as a hard disk or a printer.

In addition, in relation to foregoing Embodiments 1 and 2, process procedures of an image processing device using software based on an operation of a control unit executing a processing program, are described. However, the present invention is not limited to this, but an image processing device according to the present invention may execute process procedures using hardware.

In addition, in relation to foregoing Embodiments 1 and 2, in-vivo areas such as mucosal areas or lesion areas are described as examples of interest areas with high degree of necessity for observation. However, the present invention is not limited to this, but in-vivo areas including bubbles or excretion may be interest areas depending on contents of observation of the inside of a subject, and in-vivo areas such as mucosal areas or lesion areas (interest areas in Embodiments 1 and 2) may be non-interest areas.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device, comprising:
an interest area detector that detects interest areas included in time-series images captured in time series;
a calculation processing unit that calculates first feature amounts indicative of features of the interest areas;
an area classification unit that classifies the interest areas into area groups, based on the first feature amounts of the interest areas and the position in time for each of the captured time-series images that includes the interest areas;
an area selection unit that selects, based on second feature amounts of the interest areas in each of the area groups, one or more representative areas representing the interest areas belonging to each of the area groups, from among the interest areas belonging to each of the area groups; and
a representative image output unit that outputs one or more representative images including the representative areas in the time-series images.

2. The image processing device according to claim 1, wherein the area classification unit classifies the interest areas into area groups, based on the degree of similarity indicative of similarity in the first feature amount between the detected interest areas and a relationship in time-series position between the time-series images including the detected interest areas.

3. The image processing device according to claim 2, wherein the area classification unit includes:
an adjacent state determination unit that determines whether the interest areas detected by the interest area detector are adjacent to each other in time series; and
a degree-of-similarity determination unit that determines a degree of similarity in the first feature amount between the interest areas calculated by the calculation processing unit,
wherein the area classification unit classifies the interest areas into area groups, based on adjacent states of the plurality of interest areas determined by the adjacent state determination unit and the degree of similarity in the first feature amount in the interest areas determined by the degree-of-similarity determination unit.

4. The image processing device according to claim 3, wherein
the adjacent state determination unit determines whether the interest areas in each of area groups selected from the plurality of interest groups are adjacent or identical to each other in time series, and
if the interest areas in each of the area groups are adjacent or identical to each other in time series, the area classification unit integrates the plurality of area groups adjacent or identical to each other in time series into one area group.

5. The image processing device according to claim 1, wherein the first feature amounts of the interest areas are color feature amounts.

6. The image processing device according to claim 5, wherein
the calculation processing unit includes:
a pixel value converter that converts values of pixels belonging to the interest areas to values of L*a*b space; and
an average calculation unit that calculates averages of values of L*a*b space converted and output by the pixel value converter, as color feature amounts of the interest areas.

7. The image processing device according to claim 1, further comprising a group feature amount calculation unit that calculates a group feature amount indicative of a feature of each of the area groups based on the second feature amounts of the interest areas in each of the area groups,
wherein the group feature amount calculation unit calculates dispersion of the second feature amounts of the interest areas in a feature space formed by a coordinate axis of the second feature amounts of the interest areas and a time-series coordinate axis, and calculates the group feature amount of each of the area groups based on the calculated dispersion.

8. The image processing device according to claim 1, further comprising a group feature amount calculation unit that calculates a group feature amount indicative of a feature of each of the area groups based on the second feature amounts of the interest areas in each of the area groups,
wherein the area selection unit includes a number-of-selection decision unit that decides a number of selection (s) of the representative area(s) based on the group feature amount, and selects a number of the representative area(s) equal to the number of selection(s), from the area groups.

9. The image processing device according to claim 8, wherein the number-of-selection decision unit includes a function unit that sets a function indicative of a relationship between the group feature amounts and the number of selection(s), and decides the number of selection(s) based on the function set by the function unit.

10. The image processing device according to claim 8, wherein the area selection unit includes a sub-classification processing unit that sub-classifies the plurality of interest areas into a number of similarity group(s) equal to the number of selection(s), based on the second feature amounts of the plurality of interest areas included in the area groups, and selects one interest area for each of the similarity groups to select a number of the representative area(s) equal to the number of selection(s).

11. The image processing device according to claim 10, wherein the area selection unit includes:
a barycenter calculation unit that calculates barycenters of the second feature amounts of the plurality of interest areas included in the similarity groups for each of the similarity groups; and
a closest area selection unit that selects interest areas closest to the barycenters, from the plurality of interest areas included in the similarity groups, and
wherein the area selection unit selects the closest interest areas as the representative areas from each of the similarity groups.

12. The image processing device according to claim 8, wherein the area selection unit calculates time-series coordinates that divide distribution of the second feature amounts of the plurality of interest areas at equal distances in a time-series direction, in correspondence with the number of selection(s), and selects a number of the interest area(s) closest to the time-series coordinate(s) equal to the number of selection(s), as the representative areas from the plurality of interest areas.

13. The image processing device according to claim 1, wherein the time-series images are in-vivo images of an inside of a digestive tract of a subject captured in time series.

14. The image processing device according to claim 13, wherein the interest areas are lesion areas or mucosal areas in an inside of a body of a subject.

15. The image processing device according to claim 1, further comprising a group feature amount calculation unit that calculates a group feature amount indicative of a feature of each of the area groups based on the second feature amounts of the interest areas in each of the area groups.

16. The image processing device according to claim 1, wherein the first feature amounts are the same as the second feature amounts.

17. The image processing device according to claim 1, wherein the area classification unit classifies the interest areas into the area groups, based on a distribution state of feature amounts of the interest areas and a time-series distribution state of feature amounts of the interest areas.

18. A non-transitory computer-readable recording device with an executable program stored thereon, wherein the program instructs a processor to perform:
detecting interest areas included in time-series images captured in time series;
calculating first feature amounts indicative of features of the interest areas;
classifying the interest areas into area groups, based on the first feature amounts of the interest areas and the position in time for each of the captured time-series images that includes the interest areas;
selecting, based on second feature amounts of the interest areas in each of the area groups, one or more representative areas representing the interest areas belonging to each of the area groups, from among the interest areas belonging to each of the area groups; and
outputting one or more representative images including the representative areas in the time-series Images.

19. The non-transitory computer-readable recording device according to claim 18, wherein the program instructs the processor to perform:
classifying the interest areas into the area groups, based on a distribution state of feature amounts of the interest areas and a time-series distribution state of feature amounts of the interest areas.

20. An image processing method comprising:
detecting interest areas included in time-series images captured in time series;
calculating first feature amounts indicative of features of the interest areas;
classifying the interest areas into area groups, based on the first feature amounts of the interest areas and the position in time for each of the captured time-series images that includes the interest areas;
selecting, based on second feature amounts of the interest areas in each of the area groups, one or more representative areas representing the interest areas belonging to each of the area groups, from among the interest areas belonging to each of the area groups; and
outputting one or more representative images including the representative areas in the time-series images.

21. The image processing method according to claim 20, wherein the step of classifying the interest areas into the area groups comprises:
classifying the interest areas into the area groups, based on a distribution state of feature amounts of the interest areas and a time-series distribution state of feature amounts of the interest areas.

* * * * *